(12) United States Patent
Wilson et al.

(10) Patent No.: US 7,580,137 B2
(45) Date of Patent: Aug. 25, 2009

(54) METHOD AND APPARATUS FOR DETERMINING ONE OR MORE PHYSICAL PROPERTIES OF A ROLLED SMOKING ARTICLE OR FILTER ROD

(75) Inventors: Ronald F. Wilson, Page Hill (GB); Gary J. Pitt, Newport Pagnell (GB); Timothy G. Irons, Kempston (GB); William A. H. Everitt, Commercial Road (GB)

(73) Assignee: Molins PLC, Milton Keynes (GB)

( * ) Notice: Subject to any disclaimer, the term of this patent is extended or adjusted under 35 U.S.C. 154(b) by 345 days.

(21) Appl. No.: 10/549,995

(22) PCT Filed: Mar. 19, 2004

(86) PCT No.: PCT/GB2004/001181

§ 371 (c)(1),
(2), (4) Date: Oct. 27, 2005

(87) PCT Pub. No.: WO2004/083834

PCT Pub. Date: Sep. 30, 2004

(65) Prior Publication Data

US 2006/0098214 A1    May 11, 2006

(30) Foreign Application Priority Data

Mar. 20, 2003  (GB) ................................ 0306468.0

(51) Int. Cl.
*G01B 11/04*  (2006.01)
(52) U.S. Cl. ................ 356/625; 356/426; 356/634; 356/635; 382/141; 382/143

(58) Field of Classification Search ......... 356/426–428; 382/141, 143
See application file for complete search history.

(56) References Cited

U.S. PATENT DOCUMENTS 4,645,921 A * 2/1987 Heitmann et al. ....... 250/223 R (Continued)

FOREIGN PATENT DOCUMENTS

CN      1141144 A      6/1996

(Continued)

*Primary Examiner*—Tarifur Chowdhury
*Assistant Examiner*—Tara S Pajoohi
(74) *Attorney, Agent, or Firm*—Woodard, Emhardt, Moriarty, McNett & Henry LLP

(57) ABSTRACT

A method of determining one or more physical properties of a rolled smoking article is disclosed, the method comprising disposing a rolled smoking article within a field of view, illuminating the field of view, imaging the rolled smoking article to form an image, and analyzing the image to determine one or more physical properties of the rolled smoking article. Preferably the image is a digital image, which may be electronically processed to determine the physical properties. The physical properties may include the length of the rolled smoking article, or its mean diameter, ovality, circumference, roundness or shape. Also disclosed is an apparatus for performing such method comprising imaging means defining the field of view, means for positioning a smoking article in the field of view, illuminating means for illuminating the field of view, and processing means for processing the image to determine one more physical properties.

11 Claims, 8 Drawing Sheets

U.S. PATENT DOCUMENTS

| | | | |
|---|---|---|---|
| 4,688,583 A | 8/1987 | Neri | 131/84.2 |
| 4,907,607 A | 3/1990 | Focke et al. | 131/280 |
| 4,969,551 A | 11/1990 | Heitmann et al. | 198/384 |
| 5,301,011 A | 4/1994 | Hoppe et al. | 356/385 |
| 5,347,853 A | 9/1994 | Hoppe et al. | 73/82 |
| 5,353,356 A * | 10/1994 | Waugh et al. | 382/143 |
| 5,392,359 A * | 2/1995 | Futamura et al. | 382/141 |
| 5,404,023 A | 4/1995 | Neri et al. | 250/572 |
| 5,414,270 A | 5/1995 | Henderson et al. | 250/572 |
| 5,715,843 A | 2/1998 | Hapke et al. | 131/280 |
| 5,732,147 A * | 3/1998 | Tao | 382/110 |
| 6,075,882 A | 6/2000 | Mullins et al. | 382/141 |
| 6,169,600 B1 | 1/2001 | Ludlow | 356/237.1 |
| 6,181,372 B1 | 1/2001 | Jeri et al. | 348/128 |
| 6,276,366 B1 | 8/2001 | Fuchigami et al. | 131/280 |
| 7,262,868 B2 | 8/2007 | Hapke et al. | 356/635 |
| 2005/0098744 A1 | 5/2005 | Schroder et al. | 250/559.19 |
| 2006/0033919 A1 * | 2/2006 | Moshe | 356/430 |

FOREIGN PATENT DOCUMENTS

| | | |
|---|---|---|
| EP | 0 500 301 A1 | 8/1992 |
| EP | 0 909 537 A1 | 4/1999 |
| EP | 1 023 845 A1 | 8/2000 |
| EP | 1 397 961 A1 | 3/2004 |
| EP | 1 445 576 A1 | 8/2004 |
| GB | 2 187 549 A | 9/1987 |

* cited by examiner

METHOD AND APPARATUS FOR DETERMINING ONE OR MORE PHYSICAL PROPERTIES OF A ROLLED SMOKING ARTICLE OR FILTER ROD

CROSS-REFERENCES TO RELATED APPLICATIONS

This application is a National Stage of International Application PCT/GB2004/001181, filed Mar. 19, 2004. Applicant claims foreign priority benefits under 35 U.S.C. 119(a)-(d) of the following foreign application for patent: United Kingdom Application No. 0306468.0, filed Mar. 20, 2003, which is hereby incorporated by reference in its entirety.

BACKGROUND OF THE INVENTION

The present invention relates to a method and apparatus for determining one or more physical properties of a rolled smoking article or filter rod. The present invention has particular reference to a method of determining one or more physical properties of a cigarette comprising a tobacco column and an adjacent filter section.

Modern cigarette makers are capable of producing tipped cigarettes at a rate of approximately 8,000-16,000 cigarettes per minute. According to its particular brand, a cigarette should have an accurate predetermined length and circumference. A tipped cigarette comprises a tobacco column comprising compacted, dried and shredded tobacco leaves wrapped in a rolled tube of cigarette paper and an adjacent filter section comprising a cut length of filter rod. The filter section is joined to the tobacco column by means of a piece of tipping paper which is wrapped circumferentially around the filter section to overlap the tobacco column. The filter section of a cigarette should have an accurate, predetermined length and width and, in order to ensure a consistent appearance, the length of the tipping paper ('overwrap') should also have an accurate, predetermined length. The cigarette should be substantially free of voids at the interface between the filter section and tobacco column and at the end of the tobacco column remote from the filter section. The cigarette paper should be free of ventilation holes and unwanted markings, and any printed matter, such as words, logos and the like, should be accurately positioned.

As is in the case in many manufacturing processes, there is a need to monitor continually the quality of cigarettes produced on a maker. Conventionally, cigarettes produced by a maker are sampled at random and tested for compliance with predetermined quality standards. In particular, it is common to sample cigarettes manually or automatically and to test the sampled cigarettes for length, circumference, the presence of voids or other defects and ventilation characteristics, such as the pressure drop across the cigarette and/or filter section.

Conventional, industry standard quality assurance/quality control cigarette sampling and testing techniques provide for approximately ten cigarettes to be tested every twenty minutes. In view of the great speed with which cigarettes are produced on a typical maker, this sampling and testing rate is insufficient to achieve visualisation of the process in real time.

EP 1023845 A1 (Japan Tobacco Inc) discloses cigarette testing apparatus in which a cigarette is supplied in a horizontal position from a cigarette supplying section to a weight-measuring section where the cigarette weight is measured. The cigarette ejected therefrom is transferred sequentially to a circumference measuring section, a ventilation-characteristic measuring section and a length/hardness measuring section. In the circumference measuring section, the cigarette is received on two juxtaposed rollers which cause the cigarette to rotate about its longitudinal axis. A photosensor comprising a transmitter and receiver, located respectively above and below the rollers, is used to send and receive a slit light between the transmitter and receiver in a direction perpendicular to the axis of the cigarette and to measure a slit light width blocked by the cigarette, thereby to measure the circumference (diameter) of the cigarette. In the length/hardening measuring section, the cigarette is positioned in place by regulating one end of the cigarette, and the position of the other cigarette is measure by use of a photosensor.

U.S. Pat. No. 4,907,607 A (Focke, et al.) discloses apparatus for detecting the presence of voids or other defects in cigarettes by directing light from a light source onto an end face of a cigarette and positioning a light receiver at an angle to the longitudinal axis of the cigarette for detecting light from the light source which is transmitted through at least a portion of the cigarette and exits the cigarette through points other than the end face where the light enters the cigarette.

An object of the present invention is to provide an improved method for determining one or more physical properties of a rolled smoking article or a filter rod, particularly a cigarette comprising a tobacco column and an adjacent filter section.

Another object of the present invention is to provide a method of determining one or more physical properties of a rolled smoking article or filter rod which may be executed sufficiently rapidly to allow the variation in said properties in, for example, cigarettes produced by a maker to be monitor substantially in real time.

In accordance with one aspect of the present invention, therefore, there is provided a method of determining one or more physical properties of a rolled smoking article or filter rod, said method comprising disposing a rolled smoking article or filter rod within a field of view, illuminating said field of view, imaging said rolled smoking article or filter rod within the field of view to form an image, and analysing said image to determine one of more physical properties of the rolled smoking article or filter rod.

In another aspect of the present invention there is provided apparatus for determining one or more physical properties of a rolled smoking article or filter rod, said apparatus comprising:

imaging means defining a field of view, said imaging means being adapted for imaging a rolled smoking article or filter rod in said field of view;

means for positioning a rolled smoking article or filter rod in said field of view;

illuminating means for illuminating said field of view; and processing means for processing said image to determine said one or more physical properties of a smoking article or filter rod in said field of view.

Preferably said image is a digital image. Said imaging means may comprise a digital camera; preferably a digital video-camera.

Said image may be processed electronically to determine said one or more physical properties. Thus, said processing means may comprise a computer adapted for processing said digital image electronically.

The present invention is thus characterised by forming an image of the rolled smoking article or filter rod in a field of view and processing the image of the rolled smoking article or filter rod to determine said one or more physical properties.

Whilst light of any suitable wavelength may be used for imaging the rolled smoking article or filter rod within the field of view, the rolled smoking article or filter is preferably imaged using infra-red light; more preferably near infra-red light Thus, said imaging means may comprise an infra-red digital video-camera. Preferably said digital video camera has an adjustable shutter-speed for controlling the exposure of the smoking article or filter rod within said field of view, and said imaging means may comprise means for controlling the shutter speed of the camera according to the physical property to be measured and/or the intensity of the illumination provided by said illuminating means. The camera is preferably operated in field mode in order to reduce acquisition time.

Said processing means may be adapted for repeatedly sampling the image, and in some embodiments the computer may be equipped with a frame-grabber such as a PCI frame-grabber for sampling the digital image produced by the camera and for transmitting control signals to the camera and/or said illuminating means.

Said illuminating means may be adapted to cast diffuse light onto the field of view and, in some embodiments, the imaging means may define an optical viewing major axis, and said illuminating means may comprise one or more side-lights which are positioned laterally of the optical major axis. In particular, said illuminating means may comprise two side-lights positioned on opposite sides of the optical axis.

In some embodiments, said illuminating means may comprise a back-light adapted for back-lighting a smoking article or filter rod positioned in the field of view. Said side-lights and back-light may comprise infra-red lights. Preferably, the back-light has a sufficiently high luminosity that infra-red light is transmitted through a rolled smoking article or filter rod positioned in the field of view intermediate the back-light and the imaging means. Said back-light may be adapted to produce a collimated beam.

Preferably the smoking article or filter rod is imaged against a uniformly dark background, such that the edges of the smoking article or filter rod (when viewed in profile) provide high edge contrast without becoming over-exposed.

Preferably said positioning means are adapted for positioning the rolled smoking article or filter rod within the field of view such that the longitudinal axis of the rolled smoking article or filter rod extends substantially orthogonally with respect to the optical major axis. The camera is preferably oriented such that the major axis of the image corresponds to the minor axis of the rolled smoking article or filter rod so that diameter measurements, which have the highest tolerance, are run at maximum resolution, while length measurements, which need not be measured to the same degree of accuracy, are measured at half resolution.

In some embodiments, said positioning means may comprise means for rotating a smoking article or filter rod about its axis in the field of view. Said rotating means may comprise two juxtaposed rollers, which rollers are positioned side-by-side so as to define a groove therebetween, which groove is adapted to receive said smoking article or filter rod, and means for rotating one or both of said rollers, thereby to cause said article or filter rod to rotate.

Said positioning means may comprise means for moving a smoking article or filter rod axially relative to the field of view. Preferably, the moving means comprise means for locating one end of a smoking article relative to the field of view, thereby to establish a known position against which measurements of length can be made.

Said moving means may comprise a pusher adapted to engage one end of a smoking rod or filter rod, and a linear actuator for moving said pusher along a predetermined path, and said locating means may be adapted for indicating the position of said pusher. In some embodiments, said linear actuator may comprise a servo motor for locating said pusher relative to the field of view. Alternatively, a stepper motor having an encoder may be used.

The positioning means may be calibrated by moving the pusher into the field of view, imaging the pusher within the field of view to form an image and processing the image to determine the precise position of the pusher within the field of view. That position of the pusher may be stored as a datum position, so that subsequent movement of the pusher can be related to the datum position for determining the distance between any position of the pusher and said datum position.

Said digital video-camera may comprise a photosensor adapted to form an image consisting of an array comprising a multitude of regularly arranged pixels. Said image sensor preferably comprises a charge coupled device (CCD), but may alternatively comprise any other suitable image sensor such, for example, as a CMOS sensor. Said processing means may conveniently be adapted for measuring distances in said image in terms of pixels, and may be calibrated for converting such pixel distances into actual distances. In some embodiments, said processing means may be calibrated by processing one or more images of one or more objects of accurately known dimensions. In some embodiments the imaging means may be such that the relationship between pixels and actual distances may not be truly linear owing to certain optical effects. Preferably the processing means are therefore calibrated by processing the images of a plurality of objects of different dimensions to compensate for any such non-linear optical effects.

CCD-based cameras suffer from 'blooming', whereby excessively bright (over-exposed) objects within the field of view may appear larger than their actual sizes. This effect is caused by saturated elements of the CCD array affecting nearby elements. In addition the interline transfer system employed in a CCD can produce 'vertical smearing' of saturated objects. Accordingly, it is important to ensure that the rolled smoking article or filter rod is not over-exposed. An appropriate shutter speed to use for measuring a particular physical property is preferably determined empirically.

In some embodiments, said one or more physical properties may include the length of the rolled smoking article or filter rod. The length of the rolled smoking article may be determined by moving the rolled smoking article or filter rod axially whilst locating one end thereof with respect to the field of view until the other end is disposed within the field of view, and thereafter imaging the rolled smoking article or filter rod to form said image, processing the image to locate said other end with respect of the field of view, and thereafter determining the length of the rolled smoking article or filter rod from the positions of said ends.

Preferably, the rolled smoking article or filter rod is advanced axially until said one end is located at a first predetermined position with respect to the field of view corresponding to a first nominal length of the rolled smoking article of the filter rod, and the other end is disposed within the field of view in the vicinity of a first nominal position corresponding to said first nominal length. The image may then be processed to determine the actual position of the other end, and the length of the rolled smoking article or filter rod calculated by determining the difference between said first nominal and actual positions and adding or subtracting that difference to or from the first nominal length. Said image may be processed within a first region of interest within said field of view, which first region of interest encompasses all likely actual positions of said other end of the rolled smoking article or filter rod when said one end is located at said first predetermined position. By limiting processing of the image to the first region of interest in which said other end of the rolled smoking article or filter rod is expected to be disposed, the image can be processed more quickly, without having to process the entire image of the field of view. The position of said other end may be calculated using horizontal and vertical region projections of said region of interest; the resulting projections may be analysed in order to detect any significant edges within the region of interest, which will correspond to said other end. The same technique may be used for detecting other edges as described below.

Thus, the apparatus in accordance with the present invention may further comprise control means for controlling said moving means and said processing means, said control means comprising a database adapted to store a first nominal length for the rolled smoking article or filter rod and being adapted to control said moving means to move the one end of the rolled smoking article or filter rod to a first predetermined position with respect to the field of view corresponding to the first nominal length, such that the other end is disposed within the field of view, and thereafter to control the processing means to process the image to locate said other end with respect of the field of view and to determine the actual length of the rolled smoking article or rod from the locations of said one and other ends.

Preferably said control means are adapted to derive a first nominal position for said other end within the field of view when the one end is positioned at the first predetermined position, said first nominal position corresponding to said first nominal length, and said processing means may be adapted to locate the actual position of the other end and calculate the difference between the actual and nominal positions, the length of the rolled smoking article or filter rod being equal to the first nominal length plus or minus the difference. Said control means may further be adapted to derive a first predetermined region of interest in the field of view, which encompasses all likely positions of the other end of the rolled smoking article or filter rod, when said one end is positioned at the first predetermined position, and said processing means may be controlled to process said image within the first predetermined region of interest to locate said other end.

Known image-processing techniques may be used for processing the image to determine accurately the position of the other end of the rolled smoking article or filter rod in the field of view. Those skilled in the art are familiar with image processing algorithms for detecting edges in digital images, including algorithms which measure contrast levels for defining a point at which an edge is defined as being present, the length (in pixels) along an edge which is used to determine a contiguous and true edge, and algorithms for carrying out statistical probability calculations to confirm (or otherwise) that a detected edge is a true edge. As described above, a preferred technique for detecting the position of a feature within a region of interest comprises generating horizontal and vertical region projections of a region of interest, and then analysing said projections in order to detect any significant edges within the region of interest, which will correspond to the feature being measured. Such imaging processing techniques are not described further herein, but are described in detail in a number of standard reference works including Sonka, et al., 1999, *Image Processing, Analysis, and Machine Vision*, $2^{nd}$ Edition, page 256 (6.35), Pacific Grove: PWS Publishing, ISBN 0-534-95393-X, the contents of which are incorporated herein by reference. By imaging the rolled smoking article or filter rod against a dark background, relatively fast shutter speeds can be used for acquiring images for detecting external edges such as said other end, thereby avoiding or reducing any undesirable blooming effect. An appropriate shutter speed should be determined empirically on a product sample to avoid over-exposure.

In some embodiments, said rolled smoking article or filter rod may comprise one or more intended visible external features intermediate its opposite longitudinal ends, the or each feature having a different colour of shade from the immediately adjacent portion or portions of the article or rod, rendering the edge of edges of the or each feature visible by contrast with said adjacent portion(s). It is generally desirable that such intended features should be positioned accurately on the article or rod, and the position of such a feature is usually specified by reference to a reference end of the article or rod. A rolled smoking article typically has first and second adjacent longitudinal sections and an outer tipping layer which extends axially from a first end of the rolled smoking article over one of said first and second sections and overlaps the interface between said sections to cover partially the other section, said outer tipping layer terminating remote from said first end in an edge. The length of the overwrap is usually specified by reference to the first end and is thus equal to the distance between said first end and the edge. Said outer layer may have a significantly different colour or shade from the other section, rendering said edge visible. A cigarette, for example, typically comprises a first tobacco column and a second adjacent filter section and an outer layer of tipping paper which extends from the first end of the cigarette over the filter section to overlap the interface between the tobacco column and filter section to cover partially the tobacco column. Said outer tipping layer commonly has a different colour from the first tobacco section. A smoking article or filter rod may also comprise printed matter on its outer surface between said opposite ends, such as one or more letters, numerals, words, logotypes, and the like, or a combination of these, which matter may be printed using one or more inks having a different colour or shade from the immediately adjacent portion(s) of the article or rod, rendering the edge or edges of the printed matter visible by contrast.

In accordance with the present invention, said image may be processed to determine the axial position or positions of one or more such external features with respect to a pre-specified reference end of the rolled smoking article or filter rod.

The axial position of such an external feature may be determined in accordance with the present invention by determining the axial orientation of the rolled smoking article or filter rod with respect to said reference end, advancing the rolled smoking article or filter rod axially whilst locating said one end thereof with respect to the field of view until the feature is disposed within the field of view, imaging said rolled smoking article or filter rod to form said image, processing the image to locate said feature with respect to the field of view, and thereafter determining the axial position of the feature with respect to said reference end from the position of the edge, the position of said one end and, depending on the axial orientation of the rolled smoking article or filter rod, the length of the rolled smoking article or filter rod.

Preferably, the rolled smoking article or filter rod is advanced axially until said one end is located at a second predetermined position with respect to the field of view corresponding to a first nominal distance between said feature and the one end of the rolled smoking article or filter rod, and the feature is disposed within said field of view within the vicinity of a second nominal position corresponding to said first nominal distance. Said image may be processed to determine the actual position of said feature, and the actual distance between the feature and the one end of the rolled smoking article or filter rod may be determined by calculating the difference between said second nominal and actual positions and adding or subtracting that difference to or from the first nominal distance, the axial position of the feature with respect to the reference end being equal to said actual distance or, depending on the axial orientation of the rolled smoking article or filter rod, the length of the rolled smoking article or filter rod minus the actual distance. Said image may be processed within a second limited region of interest in the field of view, which second region of interest encompasses all likely actual positions of the feature when said one end is located at said second predetermined position.

Suitably the database of the apparatus in accordance with the present invention may be further adapted to store user-inputted data indicating the axial orientation of the rolled smoking article or filter rod. A rolled smoking article or filter rod having a visible external feature between its opposite longitudinal ends may be directional, in the sense that the rolled smoking article or filter rod is rotationally asymmetrical when turned through 180° about a point mid-way between said opposite longitudinal ends. Thus, the rolled smoking article or filter rod may be conveyed by said moving means, with either of said longitudinal ends first, and for that reason said processing means may be adapted, as mentioned above, to receive user-inputted information concerning the axial orientation of a rolled smoking article or filter rod to be tested.

Said database forms an important feature of the present invention in that the physical properties of a rolled smoking article, e.g. a cigarette, or filter rod, such as its length, circumference, etc. vary from brand to brand. The database in accordance with the present invention may comprise nominal information for a plurality of different brands of cigarette, including said first nominal length and said first nominal distance, and said processing means may be adapted to receive user-inputted data identifying the particular brand of rolled smoking article or filter rod to be tested, so that the correct nominal values can be selected and used by said control means.

Thus, said database may be adapted to store a nominal axial position of said feature with respect to said reference end, and said control means may be adapted to derive from the nominal axial position and, depending on the axial orientation of the rolled smoking article or filter rod, the first nominal length, said first nominal distance between said feature and said one end of the rolled smoking article or filter rod, and to control the moving means to move the rolled smoking article or filter rod to the second predetermined position with respect to the field of view corresponding to said first nominal distance, such that said feature is disposed within the field of view, and thereafter to control said processing means to process the image to locate said feature with respect to the field of view and determine the actual axial position of the feature from the position of the feature, the position of the one end and, depending upon the orientation of the rolled smoking article, the actual length of the rolled smoking article.

Preferably, said control means are further adapted to derive from the nominal axial position and, depending on the axial orientation of the rolled smoking article or filter rod, the first nominal length, said second nominal position for said feature with respect to the field of view, when said one end is positioned at said second predetermined position, and said processing means may be adapted to locate the actual position of said feature with respect of the field of view and to determine the actual distance between said feature and said one end by calculating the difference between said actual and second nominal positions and adding or subtracting that difference to or from the first nominal distance, the actual axial position of said feature with respect to said reference end being equal to the actual distance or, depending on the orientation of the rolled smoking article or filter rod, the actual length of the rolled smoking article or filter rod minus the actual distance.

Said control means may be adapted to derive said second predetermined region of interest of said field of view which encompasses all likely positions of the feature of, when said one end is positioned at said second predetermined position, and said processing means are controlled to process said image within said second predetermined region of interest to locate said feature.

When said rolled smoking article or filter rod comprises a rolled smoking article, such for example as a cigarette, comprising an outer tipping layer that extends from said first end over one of the first and second adjacent sections to overlap the other section, said feature preferably comprises said edge of the outer tipping layer. Said first end is preferably nominated as said reference end, and the axial position of said edge with respect to said reference end is the length of the tipping layer between said first end and said edge. The nominal axial position of said edge with respect to said reference end which may be stored by said database is a second nominal length for said outer tipping layer.

Alternatively said feature may comprise printed matter on the outer surface of rolled smoking article or filter rod as described above. In particular, said feature may comprise a characteristic feature of an item of printed matter, for example a pre-defined point of character or graphic device. If the printed matter comprises a plurality of individually printed items then the axial position of each item may be determined in accordance with the present invention.

According to a particular aspect of the present invention, said processing means may be adapted for repeatedly sampling the image as a rolled smoking article or filter rod is rotated by said rotating means and for processing each image sample to measure the diameter of said rolled smoking or filter rod in each image sample and using the measurements to obtain one or more physical properties of said rolled smoking article or filter rod selected from the mean diameter, ovality, circumference, roundness and shape of said rolled smoking article or filter rod.

The diameter of the rolled smoking article or filter rod in each image sample may be obtained by processing the sample to locate the two opposite edges of the rolled smoking article or filter rod in profile and calculating the distance between said opposite edges. Each image sample may be processed within two predetermined, laterally spaced regions of interest of said field of view to locate said two opposite edges, which regions of interest are determined on the basis of a nominal diameter of the rolled smoking article or filter rod.

Said database may thus be adapted to store the nominal diameter of the rolled smoking article or filter rod, and said control means may be adapted to define said two laterally spaced regions of interest of the field of view corresponding to the nominal diameter, each of which regions of interest encompasses all likely positions of a respective one of the opposite edges, and said control means may be configured to control the processing means to process each image sample within said two regions of interest to locate said opposite edges.

Preferably the diameter of the rolled smoking article or filter rod is measured at two more axially spaced locations on said rolled smoking article or filter rod. Where the rolled smoking article or filter rod comprises a rolled smoking article comprising first and second adjacent longitudinal sections, such as a cigarette comprising a tobacco column and an adjacent filter section, it is preferred that the diameter of each section should measured separately.

Said rolled smoking article or filter rod may comprise one or more circumferential markers adapted to indicate the rotational orientation of the rolled smoking article or filter rod, and said processing step may include processing the samples to determine a complete revolution of the rolled smoking article or filter rod. Thus, said processing means may be adapted to detect one or more circumferential markers on a rolled smoking article or filter rod, and said control means may be adapted to control said rotating means in response to output from the processing means such that rolled smoking article and filter rod is rotated through a complete revolution.

In a particular aspect, the present invention comprehends determining the axial direction of a rolled smoking article which is rotationally asymmetric as described above, such that the rolled smoking article is directional and comprises at least one outer layer which is wrapped circumferentially around the rolled smoking article to overlap itself thereby to form a longitudinal seam. The image samples may be processed to determine the wrapping direction of the outer layer relative to direction of the rolled smoking article. In particular, said image sample may be processed to determine the position of the longitudinal seam by detecting the position of a shadow cast by said seam as the rolled smoking article rotates. Each image sample may be processed in accordance with the present invention to detect the presence of said shadow in two predetermined, laterally spaced regions of interest in the field of view, the presence of said shadow in one or other of said regions of interest being determinative of the direction of wrapping of the outer layer, the regions of interest having been determined on the basis of the nominal width of the rolled smoking article.

Preferably, said infra-red side-lights are arranged for illuminating said rolled smoking article obliquely to enhance the shadow cast by said seam.

Said processing means may therefore be adapted for repeatedly sampling the image as said rolled smoking article is rotated by said rotated means and processing each sample to detect the position of the shadow cast by the longitudinal seam of the outer layer. Said database may be adapted to store said nominal diameter of the rolled smoking article, said control means being adapted to derive two laterally spaced regions of interest of said field of view based on said nominal width, each of said regions of interest encompassing all likely positions of said shadow depending on the direction of wrapping of the outer layer and to control said processing means to detect the presence of the shadow in one of the regions of interest.

A rolled smoking article may comprise two or more outer layers, each of which outer layers is wrapped circumferentially around the rolled smoking article to overlap itself to form an axially extending seam, and in a particularly advantageous aspect of the present invention said image may be processed to determine the wrapping direction of each outer layer relative to the direction of rolled smoking article.

Many modern cigarette makers are adapted to manufacture cigarettes in two parallel lines. In each line, tobacco columns are formed by wrapping cigarette paper circumferentially around measured portions of tobacco. As described above, the cigarette paper is wrapped around each rod to overlap itself and form a longitudinal seam. The tobacco columns in each stream are then tipped in the conventional fashion by inserting a double-length piece of filter rod between two tobacco columns and then over-wrapping the filter rod with tipping paper to join the filter rod section to each of the tobacco columns, the filter paper overlapping each of said tobacco columns. The filter rod is then guillotined to form two complete cigarettes. The filter paper is wrapped around the filter section and two adjoining tobacco columns in opposite directions on the two lines of the maker. Accordingly, when the cigarettes are guillotined, there are four possible permutations of direction of wrapping of the cigarette paper and tipping paper.

By determining the respective directions of wrapping of the two outer layers relative to the axial direction of the rolled smoking article in accordance with the present invention, the particular line of a maker on which the rolled smoking article was made can be identified. It will be appreciated that this is important because the physical properties of cigarettes made on the two lines of the maker may vary differently with time a, and when the finished cigarettes from the two lines are sampled and tested, it is important to know from which line a given cigarette originates.

Thus, said processing means may be adapted to determine the respective wrapping directions of two or more outer layers of the rolled smoking article, each of which outer layers is wrapped circumferentially around the rolled smoking article to overlap itself to form an axially extending seam.

In addition to intended visible external features which are positioned with reference to a reference end, a rolled smoking article or filter rod may also comprise one or more intended visible external patterns which are not positioned with respect to such a reference end, but comprise a regularly repeating design, said design comprising one or more features which are visible by contrast with the immediately adjacent portions of the rolled smoking article or filter rod. For example, the cigarette paper used to wrap a tobacco column often comprises a plurality of regularly axially spaced, circumferential, relatively dark bands of prescribed thickness and spacing. Typically the nature of such bands is characteristic of the paper and may vary from one brand or variety of cigarette to another.

In accordance with another aspect of the present invention, said processing means may be programmed to analyse said image obtained by said imaging means to locate two adjacent design repeats of such a pattern and to measure the pitch between corresponding features of the two repeats.

In some embodiments, the processing means may be programmed to measure one or more characteristic dimensions of the design between two or more features of a single design repeat.

Preferably said pitch and characteristic dimension(s) are measured axially with respect to the rolled smoking article or filter rod.

Said processing means may be further programmed to compare said pitch or characteristic dimension(s) respectively with a corresponding nominal pitch and nominal characteristic dimension(s) stored in said database and to generate an alarm signal if a measured pitch or characteristic dimension is not substantially the same as the corresponding nominal pitch or dimension within a predetermined margin of error.

For example, said processing means may be adapted to locate the respective axial positions of the two opposite edges of each of two adjacent circumferential bands on a cigarette paper of the kind described above, and to measure the pitch between corresponding edges of the two bands, and the axial thickness between the two opposite edges of the same band. A wrong pitch and/or dimension might indicate that an incorrect stock of paper has been used.

In another aspect of the present invention, said rolled smoking article or filter rod may be back-lit to reveal internal physical properties of the rolled smoking article or filter rod, and said image may be processed to determine said physical properties. As mentioned above, said rolled smoking article or filter rod is preferably back-lit with infra-red light. Said processing means may be adapted to detect any voids in the rolled smoking article or filter rod, said voids may be apparent in the image as areas of unusually greater brightness where the translucency of the rolled smoking article or filter rod is increased owing to the absence or dearth of tobacco or filter material in the void. Since the back-light is able to penetrate paper easily, the camera may be set to a relatively fast shutter speed for the detection of voids. Voids may be detected in the image as bright spots using basic segmentation as disclosed by Sonka, et al., 1999, ibid at pages 124-128, after the image has been 'thresholded' using a bimodal histogram threshold detection algorithm as described by Ridler, et al. in Picture Thresholding Using an Iterative Selection Method, *IEEE Transactions on Systems, Man and Cybernetics,* 1978; 8(8): 630-632.

Said rolled smoking article or filter rod may comprise a rolled smoking article having a tobacco column and an adjacent filter section, and for the majority of kinds of filter rod, said rolled smoking article may be illuminated to show an internal end face of filter section at the interface between said column and said section, and said image may be processed to determine the length of the filter section between said end face and the other end of the filter section at the end of the rolled smoking article. This operation requires very low shutter speeds, such that as much light as possible is able to penetrate the filter rod. This may lead to some overexposure of the image; however, the inaccuracies caused by any apparent blooming of the image are expected to lie within required tolerances for this measurement. Vertical smearing is not significant due to the projection technique used to locate edges within an image.

It will be appreciated that the internal end face of the filter section is a feature which is visible externally when the rolled smoking article is back-lit, and thus the axial position of said end face with respect to said other end of the filter section, which is the length of the filter section, may be determined substantially as described above. Thus the length of the filter section between the internal end face and said other end may be determined by determining the axial orientation of the rolled smoking article, moving the rolled smoking article axially whilst locating one end thereof with respect of the field of view until the end face is disposed within the field of view, imaging the rolled smoking article to form said image, processing the image to locate said internal end face with respect to the field of view, and thereafter determining the length of the filter section from the positions of the one end and of the end face and, depending on the orientation of the rolled smoking article, on the length of the rolled smoking article.

Preferably the rolled smoking article is advanced axially until the one end is located at a third predetermined position with respect to the field of view corresponding to a second nominal distance of the internal end face from said one end, and the internal end face is disposed within the field of view in the vicinity of a third nominal position corresponding to said second nominal distance. The image may then be processed to determine the actual position of the internal end face and thus the actual distance between said internal end face and the one end by calculating the difference between the third nominal and actual positions and adding or subtracting that difference to or from the second nominal distance, the length of the filter section being equal to the said actual distance or, depending on the axial orientation of the rolled smoking article, the length of the rolled smoking article minus the actual distance.

Said image may be processed within a third limited region of interest of the field of view, which third region of interest encompasses all likely positions of the internal end face when said one end is located at said third predetermined position relative to said field of view or said datum position.

Said database may therefore be adapted further to store a third nominal length of the filter section, and the control means may be configured to derive from the third nominal length and, depending on the axial orientation of the rolled smoking article as indicated by user-inputted data, the first nominal length, a second nominal distance between an internal end face of the filter section at the interface between said filter section and said tobacco column and said one end of the rolled smoking article, and to control the moving means to move the rolled smoking article to the third predetermined position with respect to the field of view corresponding to the second nominal distance such that said internal end face is disposed within said field of view, and thereafter to control said processing means to process said image to locate said internal end face with respect of the said field of view and determine the actual length of the filter section from the position of the internal end face, the position of the one end and, depending upon the orientation of the rolled smoking article, the actual length of the rolled smoking article.

Preferably said control means are further adapted to derive from said third nominal length and, depending on the axial orientation of the rolled smoking article, the first nominal length a third nominal position for said internal end face with respect to the field of view when said one end is positioned at said third predetermined position and said processing means are adapted to locate the actual position of the internal end face with respect of the field of view and determine the actual distance between the internal end face and said one end by calculating the difference between the actual and third nominal positions and adding or subtracting that difference to or from the second nominal distance, the actual length of the filter section being equal to the actual distance or, depending on the orientation of the rolled smoking article, the actual length of the rolled smoking article minus the actual distance.

Said control means may be further adapted to derive a third predetermined region of interest of said field of view which encompasses all likely positions of the internal end face, when said one end is positioned at said third predetermined position, and said processing means may be controlled to process said image within said third predetermined region of interest to locate said internal end face.

In some embodiments, as described above, said rolled smoking article may further comprise an outer tipping layer extending axially from said first end of the rolled smoking article over said second filter section and including an overlapping portion that overlaps the interface between said tobacco section and said tobacco column to cover partially the tobacco column, and said image may be processed to determine the axial length of said outer tipping layer (the 'overwrap') and the length of said overlapping portion (the 'overlap') may be calculated from the difference between the overwrap and the length of the filter section.

Thus said processing means may be further adapted to determine the axial length of the outer tipping layer which extends axially form the first end of the rolled smoking article over the second filter section and includes an overlapping portion that overlaps the interface between the filter section and the tobacco column to cover partially the tobacco column and has an appearance which is distinct from that of the remaining non-overlapped portion of the first section, thereby to determine the length of the overlapping portion by calculating the difference between the length of the outer tipping layer and the length of the filter section.

In another aspect of the present invention there is provided apparatus for determining one or more physical properties of a rolled smoking article having a tobacco column, an adjacent filter section, an outer layer being wrapped circumferentially around said tobacco column to overlap itself thereby to form a first longitudinal seam, and an outer tipping layer, said tipping layer being wrapped circumferentially around said rolled smoking article to overlap itself thereby to form a second longitudinal seam and extending axially form a first end of the rolled smoking article over said filter section, overlapping the interface between said filter section and said tobacco column to cover partially the tobacco column and terminating remote from the first end in an edge, and having an appearance that is distinct from that of the remaining non-overlapped portion of the tobacco column, said apparatus comprising:

imaging means defining a field of view, said imaging means being adapted for forming a digital image of said rolled smoking article in said field of view;

positioning means for positioning said rolled smoking article in said field of view, said positioning means comprising means for rotating said rolled smoking article about its axis in said field of view and means for moving said rolled smoking article axially relative to the field of view;

means for locating one end of the rolled smoking article relative to the field of view;

illuminating means which are selectively operable for casting diffuse light on to said field of view for illuminating said field of view, and/or for back-lighting the rolled smoking article positioned within the field of view;

processing means which are adapted for sampling said digital image and processing said image samples to determine one or more physical properties of the rolled smoking article in said field of view;

a database adapted to store a first nominal length of the rolled smoking article, a second nominal length of the tipping layer between the edge and the first end, a third nominal length of the filter section, and user-inputted data indicating the axial orientation of the rolled smoking article on the positioning means; and control means for controlling said moving means, said rotating means, said illuminating means and said processing means, said control means being configured to:

(i) control said moving means to move the one end of the rolled smoking article or filter rod to a first predetermined position with respect to the field of view corresponding to said first nominal length, such that the other end of the rolled smoking article is disposed within the field of view, and thereafter to control said processing means to process said image to locate said other end with respect to the field of view and to determine the actual length of the rolled smoking article from the locations of said one and other ends;

(ii) control the processing means to process the image to locate two opposite edges of the rolled smoking article in profile and to calculate the distance between said opposite edges;

(iii) derive from said second nominal length and, depending on the axial orientation of the rolled smoking article, the first nominal length, a first nominal distance between said edge and said one end of the rolled smoking article, and to control the moving means to move the rolled smoking article to a second predetermined position with respect to said field of view, corresponding to said first nominal distance, such that said edge is disposed within said field of view, and thereafter to control said processing means to process said image to locate said edge with respect to said field of view and determine the actual length of the tipping layer from the position of the edge, the position of the one end and, depending on the orientation of the rolled smoking article, the actual length of the rolled smoking article;

(iv) control said rotating means to rotate said rolled smoking article about its axis and to control said processing means to sample repeatedly said image as said rolled smoking article is rotated and to process each sample to detect the position of a shadow cast by the first longitudinal seam of said outer layer, thereby to determine the direction of wrapping of said outer layer relative to the direction of the rolled smoking article;

(v) control said rotating means to rotate said rolled smoking article about its axis and to control said processing means to sample repeatedly said image as said rolled smoking article is rotated and to process each sample to detect the position of a shadow cast by the second longitudinal seam of the tipping layer, thereby to determine the direction of the wrapping of the tipping layer relative to the direction of the rolled smoking article;

(vi) derive from the third nominal length and, depending upon the axial orientation of the rolled smoking article, the first nominal length, a second nominal distance between an internal end face of a filter section at the interface between said filter section and said tobacco column and said one end of the rolled smoking article, and to control the moving means to move the rolled smoking article to a third predetermined position with respect to the field of view corresponding to said second nominal distance, such that said internal end face is disposed within said field of view and thereafter to control the processing means to process the image to locate said internal end face with respective to the field of view and determine the actual length of the filter section from the position of the internal end face and, depending on the orientation of the rolled smoking article, the actual length of the rolled smoking article; and (vii) control said processing means to determine the axial length of the overlapping portion of the tipping layer by calculating the difference between the length of the outer tipping layer and the length of the filter section.

Preferably said moving means may comprise a pusher which is adapted to engage said one end of the rolled smoking article for pushing said rolled smoking article axially relative to the field of view. Said apparatus may be calibrated to establish a datum position of said pusher relative to the field of view, and said first, second and third predetermined positions may be specified by reference to the datum position.

In addition to intended visible external features, a rolled smoking article or filter rod may undesirably comprise unwanted visible external features such as spot marks and ventilation holes. Such features may be revealed in said image of the rolled smoking article or filter rod obtained by said imaging means as one or more discreet dark areas in contrast to the surrounding areas of the rolled smoking article or filter rod, and may appear at random positions.

In accordance with another aspect of the present invention said processing means may be adapted to detect the presence of one or more unwanted visible external features by generating a contrast map for a region of said rolled smoking article or filter rod, comparing said contrast map with a reference contrast map for said region, and identifying any unexpected areas of significantly different contrast.

An unwanted visible external feature may be identified as an unexpected area of significantly greater contrast than a corresponding area of the reference map.

In some embodiments, a plurality of contrast maps of said rolled smoking article or filter rod may be generated serially as the rolled smoking article or filter rod is moved by said moving means through, or rotated by said rotating means in, the field of view of said imaging means, and each map may be compared with a corresponding reference map.

Said database may store said reference contrast maps. Preferably, said database stores a representative contrast map for each different kind of region of said rolled smoking article. Thus the database does not need to store a reference map for the whole smoking article or filter rod, but where a smoking article comprises a plurality of adjacent sections of different colour or shade, or having a different pattern, for example, the database may comprise representative a reference contrast map for each section.

In yet another aspect of the present invention, there is provided a method of monitoring the variation in physical properties of cigarettes produced on a maker substantially in real-time by serially sampling cigarettes produced by said maker and determining one or more physical properties of said serially sampled cigarettes in accordance with the present invention. The values of said one or more physical properties may be output with respect to the time of sampling and may be used, for example, to generate a graphical display of the variation of said one or more physical properties with time in cigarettes produced by the maker. Where said maker comprises two lines of cigarettes which are merged prior to packaging, the present invention comprehends serially sampling cigarettes from said merged lines and determining inter alia from the respective directions of wrapping of the said tipping and cigarette papers the line on which a given cigarette was made and associating the one or more physical properties of the cigarette with that line.

BRIEF SUMMARY OF THE INVENTION

An apparatus for determining one or more physical properties of a rolled smoking article or filter rod according to a typical embodiment includes an imaging device defining a field of view, the imaging device being adapted to image a rolled smoking article or filter rod in the field of view, a positioning unit which positions a smoking article or filter rod in the field of view such that the axis of the smoking article or filter rod is substantially orthogonal to the optical axis of the imaging device, an illuminating unit which illuminates the field of view, and a processor which processes the image to determine one or more physical properties of a smoking article or filter rod in the field of view, wherein the processor is adapted to determine one or more physical properties of the smoking article or filter rod which relate to the diameter of the smoking article or filter rod.

Following is a description by way of example only with reference to the accompanying drawings of embodiments of the present invention.

DETAILED DESCRIPTION OF THE INVENTION

Figure 1:
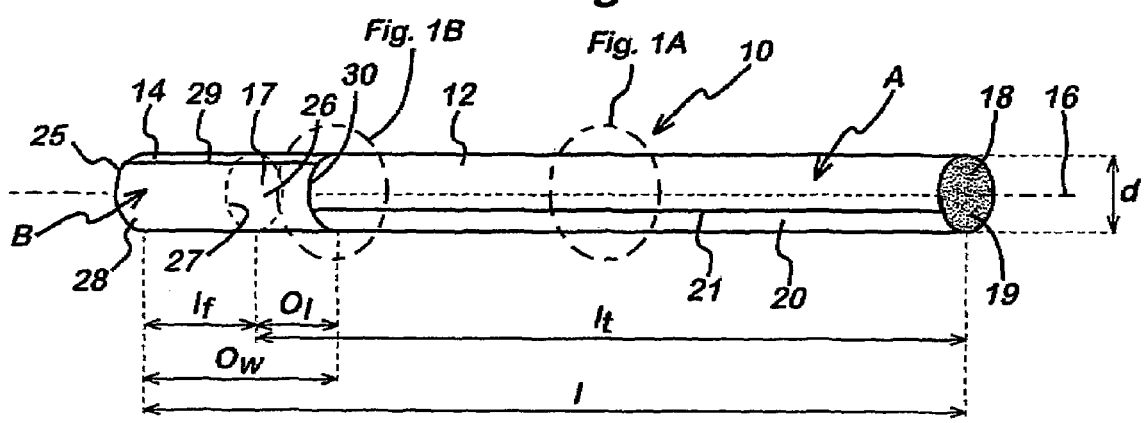
FIG. 1 is a schematic diagram of a cigarette showing various physical properties of the cigarette.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention is concerned with the automated measurement of one or more physical properties of a rolled smoking article or filter rod, particularly a cigarette. A conventional cigarette 10 is illustrated in FIG. 1. The cigarette 10 comprises a tobacco column 12 and an adjacent filter section 14. The cigarette 10 defines a longitudinal major axis 16 and has a substantially uniform diameter (d). The tobacco column 12 has first and second opposite, longitudinal ends 17, 18 and comprises compacted cut and dried tobacco leaves 19 which are enveloped within a tube of cigarette paper 20. Said tube is formed from a piece of combustible cigarette paper which is rolled circumferentially around the tobacco column 12 to overlap itself and form a first longitudinal seam 21. The second filter section 14 comprises a cut piece of filter rod having first and second opposite ends 25, 26. The second end 25 of the filter rod is disposed closely adjacent the first end 17 of the tobacco column 12 such that one internal end face 27 of the filter rod abuts the first end 17 of the tobacco column 12. In order to secure the filter rod to the tobacco column 12, a second piece of tipping paper 28 is wrapped circumferentially around the filter section 14 to overlap itself and form a second longitudinal seam 29. Said second piece of tipping paper 28 extends from the first end 25 of the filter section 14 and overlaps the interface between the filter section and tobacco column 12 to cover partially the tobacco column 12 as shown in FIG. 1. The tipping paper 28 terminates remote from the first end 25 of the filter section in a circumferential edge 30. The length of the tipping paper 28 from the first end 25 to the edge 30 is commonly called the "overwrap" ($O_w$), and the extent to which the tipping paper 28 overlaps the tobacco column 12 is commonly referred to as the "overlap" ($O_l$).

Figure 1A:
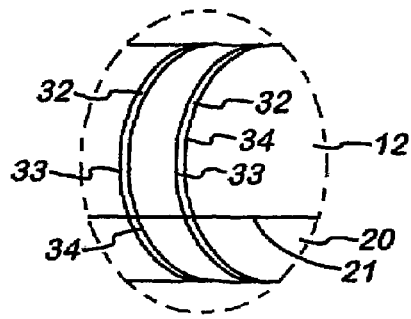
FIG. 1A is a first enlarged view of part of the cigarette of FIG. 1.
Figure 1B:
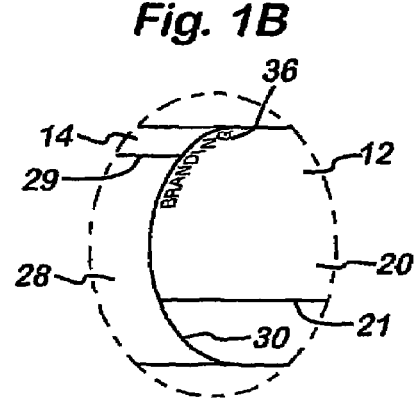
FIG. 1B is a second enlarged view of another part of the cigarette of FIG. 1.

The cigarette paper 20 generally has a pale colour, usually white or off-white, and is commonly produced with a plurality of regularly spaced, uniform stripes which have a slightly darker colour or shade than the rest of the paper. In a manufactured cigarette, said stripes form axially spaced, circumferential bands 32 around the tobacco column 12, as shown in FIG. 1A, each band having first and second opposite edges 33, 34. The thickness and spacing of said bands 32 is generally characteristic of the brand of cigarette. The cigarette paper may also be over-printed juxtaposed said edge 30 by printed matter, for example as shown in FIG. 1B. Said printed matter may comprise a plurality of alphanumeric characters and/or a logotype, generally to designate the brand of cigarette, and is usually oriented circumferentially with respect of to the axis 16 of the cigarette 10.

The tipping paper 28 around the filter section 14 may have a darker tone than the cigarette paper 20, conventionally a pale brown colour, such that said edge 30 is visible as an external feature of the cigarette 10.

The cigarette 10 is thus directional, in the sense that the cigarette 10 is rotationally asymmetrical about its mid-way point between the first end 25 of the filter section and the second end 18 of the tobacco column. The first and second pieces of paper 20, 28 may be wrapped independently clockwise or anti-clockwise relative to the direction of the cigarette 10 according to the manufacture of the cigarette. A modern cigarette maker typically comprises two parallel streams of tobacco rods; in each stream the cigarette paper 20 is wrapped around the tobacco. The tobacco columns are tipped in the conventional manner by inserting a double-length piece of filter rod between two tobacco columns, and the filter rod and adjoining tobacco columns are then overwrapped with a single piece of tipping paper 28 from a first bobbin. The double-length of filter rod is then severed in two to form two separate cigarettes. The tobacco columns on the other line are tipped, over-wrapped and cut in the same way, using tipping paper from a second bobbin which wraps tipping paper around the double-length filter rod and adjoining tobacco columns in the opposite direction to the direction of wrapping of the first bobbin. The cigarettes from the two lines are then merged for packaging. There are, therefore, four different permutations of the directions of wrapping of the cigarette and filter papers relative to the axial direction of each cigarette. Specifically, the cigarette paper 20 may be wrapped clockwise or counter-clockwise around the tobacco column 12 relative to the direction of the cigarette 10, and the tipping paper 28 may be overwrapped in the same or opposite direction from the cigarette paper 20.

The diameter (d) of a cigarette varies from brand to brand but is typically in the range of about 4.9 to 8.3 mm Typically, the circumference (c) of a cigarette varies from about 15.5 mm to about 26.00 mm The total length (tobacco column 12 plus filter section 14) (l) also varies from brand to brand in the range about 50.0 to about 125.0 mm, with the length of the filter section 14 ($l_f$) being in the range of about 16.0 to about 45.0 mm. The over-lap ($O_l$) may be in the range 1 to 20 mm.

The apparatus illustrated in FIGS. 2 to 5 of the drawings is adapted to determine inter alia one of more of the above-defined physical properties of a rolled smoking article or filter rod, such for example as a cigarette 10 of the kind described above. In particular, the apparatus in accordance with the present invention is adapted to determine the total length (l), filter length ($l_f$), over-wrap ($O_w$), over-lap ($O_l$) and diameter (d) of a cigarette 10, and also the respective directions of wrapping of the first cigarette paper 20 and second tipping paper 28. The apparatus in accordance with the present invention may also be configured to determine other physical properties of a cigarette 10, including the circumference, shape, ovality and roundness (as defined below) and to detect defects in the cigarette 10 such, for example, as voids at the interface between the tobacco column and filter section 12, 14, voids respectively at the second end 18 of the tobacco column 12 or first end 25 of the filter section 14, unwanted spot marks or ventilation holes, misaligned overprinting on the cigarette paper or overwrap, or the use of incorrect paper for wrapping the cigarette column.

Figure 2:
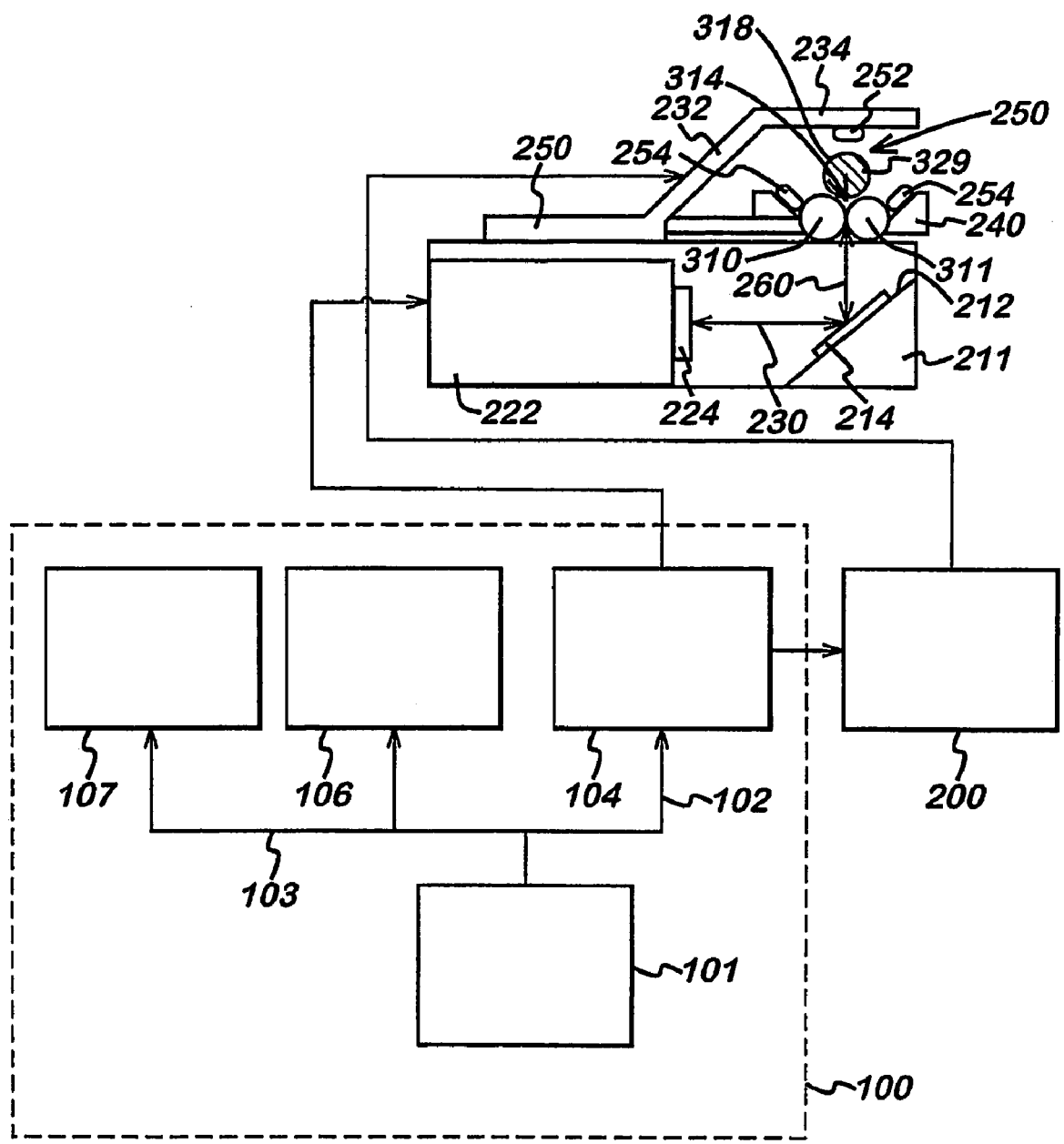
FIG. 2 is a schematic block diagram of apparatus in accordance with the present invention for measuring one or more physical properties of a rolled smoking article or filter rod, particularly a cigarette.

With reference to FIG. 2, the apparatus in accordance with present invention comprises a control system 100 comprising a conventional computer 101 comprising a microprocessor, a suitable memory device, a data storage device (such as a hard disk drive and/or CD-Rom drive), one or more data-input/output devices, an optional display device, and application software. Said one or more data input devices may comprise a conventional keyboard to enable an operator to input data, and the optional display device may comprise a conventional screen.

The computer 101 has a PCI bus 102 which connects the computer 101 to a frame-grabber device 104 which is adapted to receive and capture a video signal from an external video-camera 222 at a predetermined frame rate and to output control signals. The frame-grabber 104 is also connected to an infra-red vision system 200 as described in more detail below.

The computer 101 also has an ISA bus 103 which is connected to a motion controller 106 and to a digital output card 107 comprising a mechanical relay, both of which are connected to a rod transport system 300 also described in more detail below.

As is normal in any computer-based equipment, the control system 100 is adapted to process data for controlling the PCI frame-grabber 104, motion controller 106 and digital output card 107 and for providing a desired output in accordance with the application software which may be temporarily installed in the memory device of the computer 101 via the data storage device.

Figure 3:
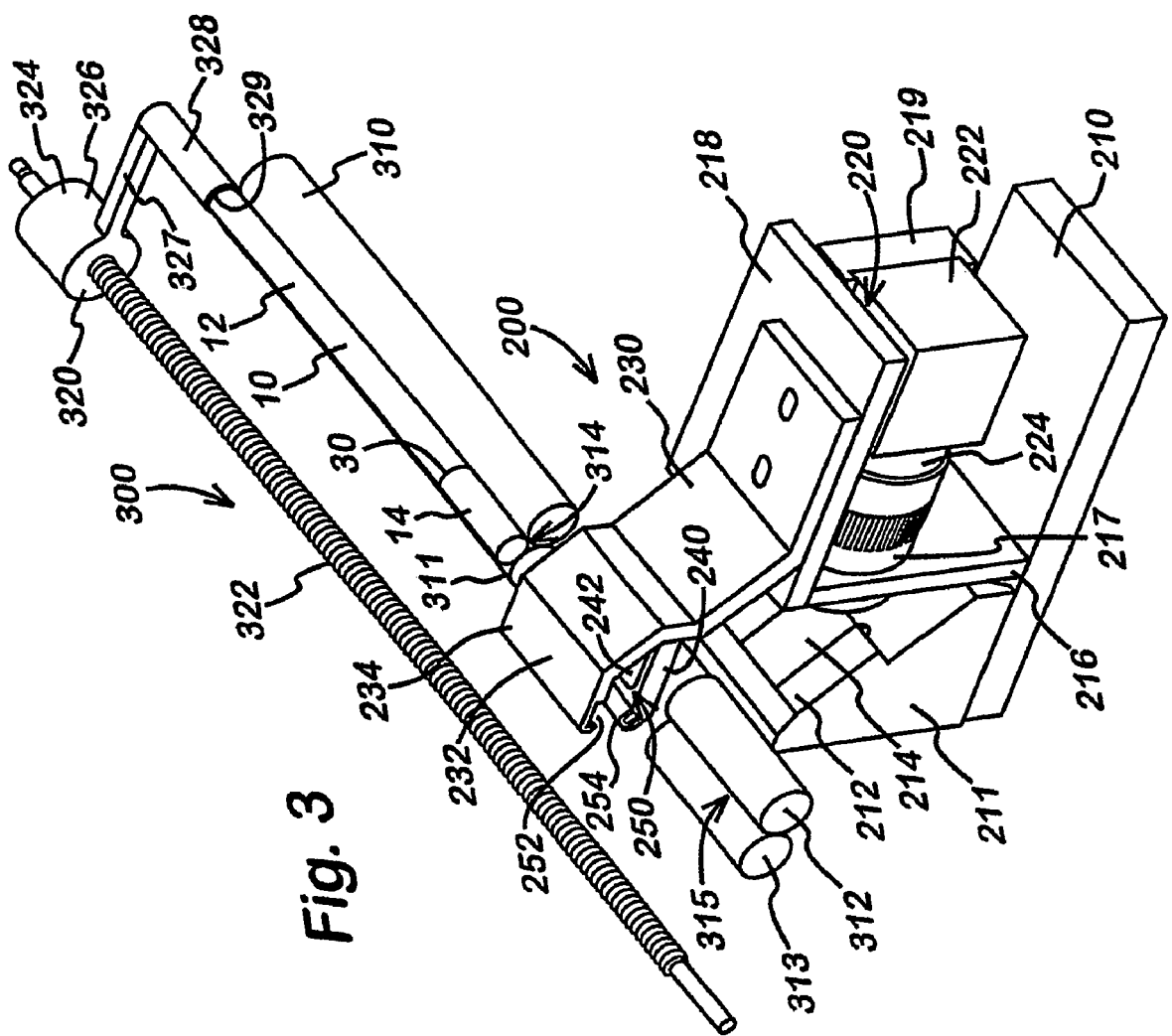
FIG. 3 is a perspective view of a transport system and vision system forming part of the apparatus of FIG. 2.
Figure 4:
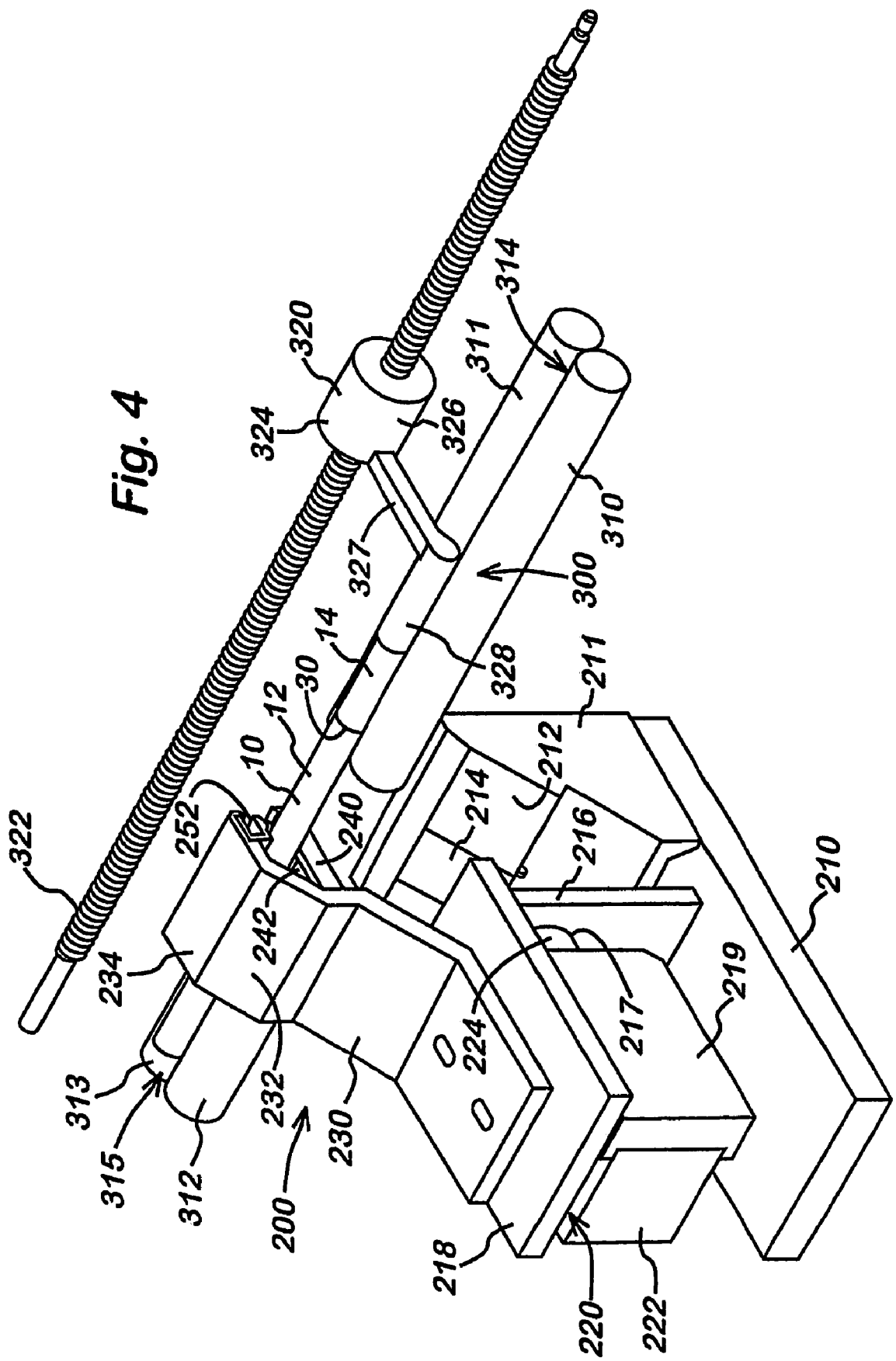
FIG. 4 is another perspective view of the vision system and transport system of FIG. 3.
Figure 5:
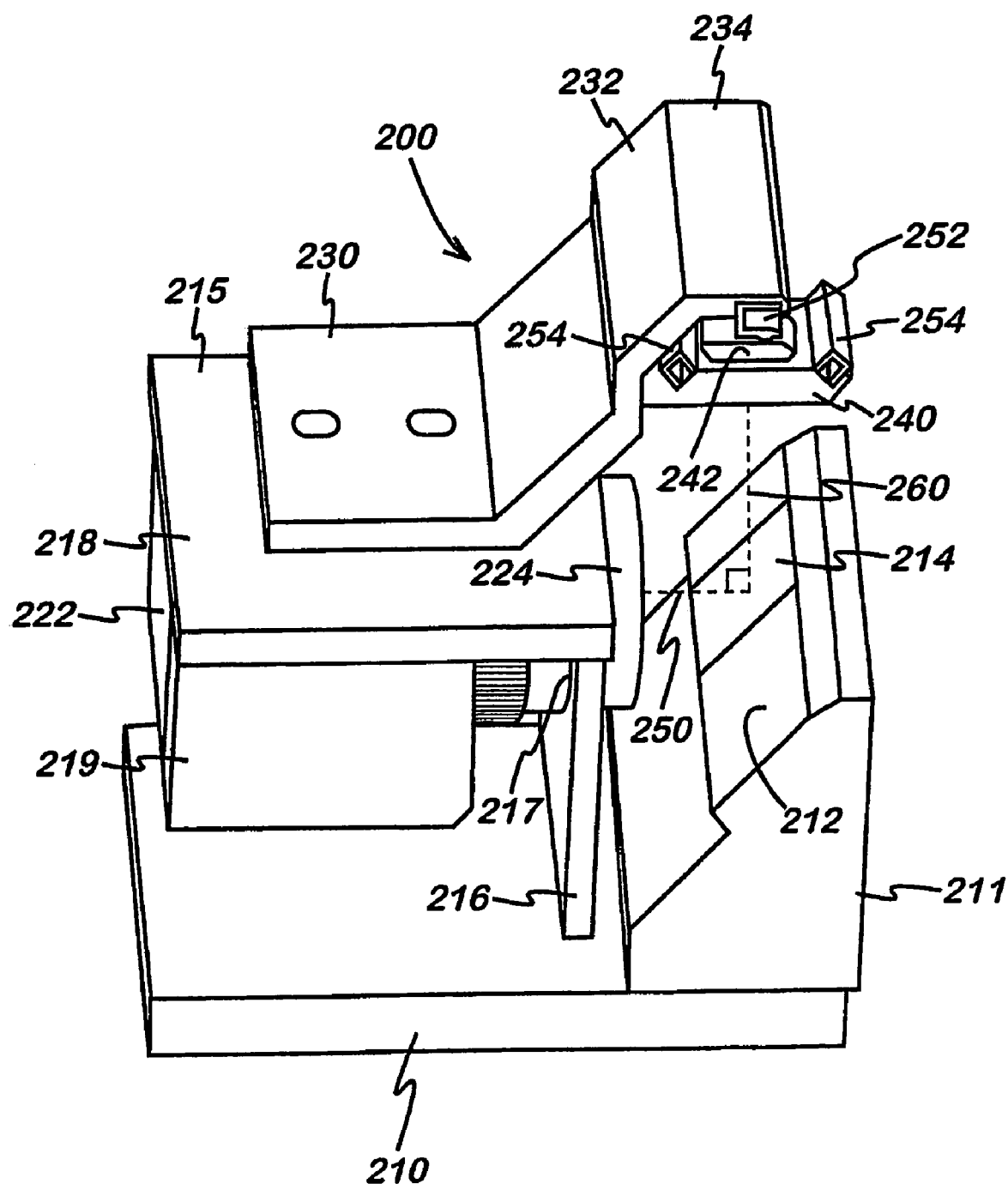
FIG. 5 is another perspective view of the vision system of FIG. 2.

With reference to FIGS. 3 to 5, the vision system 200 of the apparatus in accordance with the present invention comprises a mounting block 210 which is adapted for mounting the vision system 200 to a work bench or rig (not shown). At a front end the mounting block 210 carries an upstanding piece 211 of generally triangular cross-section having an inclined face 212 which faces rearwardly towards the opposite end of the block 210. Said inclined face 212 subtends an angle of about 45° to the upper surface of the mounting block 210 and carries a mirror 214 thereon.

Juxtaposed the upstanding piece 211, the mounting block 210 also carries a camera-mounting assembly 215. Said camera-mounting assembly 215 comprises a substantially vertically extending plate 216 which is attached to the upper surface of the mounting block 210 just rearwardly of said piece 211. Said plate 216 is formed with a generally circular orifice 217 generally opposite the mirror 214. At its upper end, the vertically extending plate 216 carries a substantially horizontally extending second plate 218 which extends rearwardly away from the upstanding piece 211 towards said rear end of the mounting block 210. At one side, the horizontally extending plate 218 carries a side plate 219. Said vertically extending first plate 216, second horizontally extending plate 218 and side plate 219 define a rectilinear recess 220 which accommodates a digital infra-red video-camera 222. Said video-camera 222 is removably secured to the plates 216, 218, 219 by suitable means (not shown) and has a cylindrical barrel 224 which extends forwardly through the aperture 217 in the first plate 216 towards the mirror 214 on the upstanding piece 211. Said barrel 224 defines a first major optical axis 230 as best seen in FIG. 2.

Said video-camera 222 is sensitive to near infrared light and comprises a single double-convex (DCX) lens housed within said barrel, which lens has a focal length of 30 mm to ensure that all brands of cigarette within the anticipated diameter range can be viewed at a resolution of 0.01 mm. Preferably, the camera 222 comprises a charge coupled device (CCD), although a CMOS photosensor may also be used. The CCD sensor is adapted to form a digitised image of an object consisting of an array comprising a multitude of regularly arranged pixels. The camera operates in field mode (to reduce acquisition time) at a resolution of 768×247, and has a video output which is connected to the frame-grabber 104 of the computer control system 100.

The camera 222 comprises an auto-focussing device (not shown) which can be controlled remotely by said control system 100. In a presently preferred embodiment, a gear is cut into the outside of the lens barrel 224, which gear is driven by a toothed belt from a DC motor controlled by said control system 100. Said auto-focussing device is adapted to allow the focal length of said camera to be adjusted step-wise between two extremes ($f_1$, $f_N$) and typically comprises an auto-focussing servo-motor for selectively driving said auto-focussing device between said extremes. The precise number of integer steps (N) between said extremes may vary from one embodiment to another, but typically the device comprise 100 (N=100) positions between said extremes. The shutter speed of the camera 222 can be set by the application software as described below.

On its upper surface, the horizontally extending second plate 218 carries a shaped bracket 230 having an angled portion 232 which extends upwardly and forwardly over the space between the first vertically extending plate 216 and the inclined face 212 of the upstanding piece 211. At its upper end, the angled portion 232 comprises an upper substantially horizontal portion 234. At its lower end, the angled portion 232 carries a forwardly directed jig member 240 which extends below the upper portion 234 over the space between the first vertically extending plate 216 and the upstanding piece 211.

As best seen in FIG. 5, the jig member 240 is generally rectangular in plan view and has a central, generally square aperture 242 formed therein. With reference to FIG. 2, the aperture 242 is aligned with the mirror 214 to define a second optical major axis 260 such that a notional beam of light extending downwardly through the aperture 242 onto the mirror 214 is reflected through a right angle 214 by the mirror onto the first optical axis 230 of the camera 222. The jig member 240 and upper portion 234 of the bracket 230 define therebetween an object space 250 which is adapted to receive a cigarette 10 to be imaged as described in more detail below.

The underside of the upper portion 234 forms a background for the object space and is uniformly dark to give good contrast with a smoking article or filter rod to be imaged. Said underside carries an infra-red back-light 252 which is selectively operable to emit a 3 mm wide collimated beam, and the jig member 240 carries two diffuse infra-red side-lights 254 which are positioned on opposite sides of the aperture 242, obliquely of the second optical axis 260 which extends through the aperture 242 to the mirror 214 substantially at right angles to the first optical axis 230 as described above. The infra-red back-light 252 and infra-red side-lights 254 are connected to a power control box 255 which is adapted to receive control signals from the frame-grabber 104.

Said transport system 300 comprises two pairs of juxtaposed rollers 310, 311, and 312, 313. Each pair of juxtaposed rollers is disposed to a respective side of the mounting block 210 and extends substantially horizontally at approximately the same level as the jig member 240. Each pair of rollers defines an upper groove 314, 315 which is adapted to receive slidingly a cigarette 10 as shown in FIGS. 3 and 4, such that the longitudinal axis of the cigarette 10 is oriented substantially orthogonally to the second optical major axis. The grooves 314, 315 defined by the two pairs of juxtaposed rollers are aligned with one another and are disposed at substantially the same level so that a cigarette can be transferred smoothly from one pair of rollers 310, 311 to the other pair of rollers 312, 313 via the jig member 240. Said rollers 310-313 are connected to said digital output card 107 and are adapted to rotate about their respective axes when the output of said card is '1', so as to rotate a cigarette 10 disposed therein about its longitudinal axis 16, and to be stationary when the output of the card is '0'.

With reference to FIGS. 3 and 4, a linear actuator 320 is positioned juxtaposed the two pairs of rollers 310-313 for selectively pushing a cigarette 10 resting on the rollers 310-313 longitudinally along said grooves 314, 315 in succession. Said linear actuator 320 comprises an elongate lead screw 322 which is rotatably connected to a servo motor (not shown) for rotating the lead screw 322 about is axis. Said servo motor is connected to said motion controller 106 for receiving control signals from the control system 100. Said lead screw 322 carries a nut assembly 324 which is adapted to travel longitudinally along the lead screw 322 when the lead screw 322 is rotated by the servo motor. Said nut assembly 324 comprises an outer casing 326 to which is joined a short radially extending arm 327. Remote from the casing 326, the arm 327 carries an axial pusher portion 328 having a polished flat end face 329 (see FIG. 3).

Said pusher portion 328 is aligned axially with the grooves 314, 315 defined by the two pairs of juxtaposed rollers 310-313 such that upon actuation of the servo motor, the pusher portion 328 is caused to move longitudinally along said grooves 314, 315 in succession. Said end face 329 is adapted to abut one longitudinal end of a cigarette 10 received in said grooves 314, 315. Thus, movement of the pusher portion 328 is calculated to push a cigarette 10 along said grooves 314, 315. Said arm 327 is adapted to pass between the upper portion 234 of the bracket 230 and of the jig member 240, such that the pusher portion 328 can pass therebetween over the aperture 242.

Said servo motor is adapted to return a position signal to the motion controller 106 for determining the position of the pusher portion 328 relative to a predetermined datum position. Preferably, the servo motor is capable of driving the pusher portion 328 at a speed of about 300 mm per second or more.

The linear actuator 320 is thus adapted to push a cigarette 10 along the groove 314, 315 defined by the two pairs of juxtaposed 310-313 through the object space 250 which, by virtue of the mirror 214, is disposed in the field of view of the camera 222. By operating the side-lights 254, the field of view can be illuminated with diffuse light for illuminating a cigarette in the object space 250, and the back-light 252 can be used to back-light the cigarette 10. Said back-light 252 is of sufficiently high luminosity that infra-red light emitted by the back-light 252 can be transmitted through the cigarette 10 depending on the degree of opacity of the cigarette 10. The camera 222 is oriented such that the major axis of the image corresponds to the minor axis of the cigarette 10. This ensures that diameter measurements, which have the highest tolerance, are run at maximum resolution, while length measurements such as filter rod position, overwrap position, etc., which need not be measured to the same degree of accuracy, are measured at half resolution.

A cigarette 10 in the field of view of the camera 222 is thus imaged using infra-red light by the camera 222 which transmits image signals to the frame-grabber 104. Said image is sampled by the frame-grabber at a predetermined rate and the image is processed by the computer 101 in accordance with the application software to determine the physical properties of the cigarette 10 as described in more detail below. The transport system 300 is controlled by the control system 100 via the motion controller 106 to position selected parts of the cigarette 10 in the field of view for imaging.

Suitable imaging software which can be run on the computer 101 for analysing the digital image to discern one or more features in the image is well-known in the art and is not described in detail herein. Typical imaging software utilises one or more well known algorithms for detecting an edge of an object in a digital image. Such algorithms typically comprehend measuring contrast levels for defining a point at which an edge is defined as being present, and the length (in pixels) along the define edge which is used to determine a contiguous and true edge, and involve statistical considerations to determine the probability that a detected edge is a true edge. Edges are detected by analysing horizontal and vertical region projections of the image as described, for example, by Sonka, et al., 1999, *Image Processing, Analysis, and Machine Vision*, 2$^{nd}$ Edition, page 256 (6.35), Pacific Grove: PWS Publishing. ISBN 0-53495393-X, the contents of which are incorporated herein by reference. Bright spots corresponding to internal voids and the like are detected using basic segmentation as described, for example in Sonka, et al., ibid at pages 124-128, after the image has been 'thresholded' using a bimodal histogram threshold detection algorithm as taught, for example, by Ridler, et al., Picture thresholding using an iterative selection method, *IEEE Transactions on Systems, Man and Cybernetics*, 1978; 8(8): 630-632; the contents of both of which are incorporated herein by reference.

Central to operation of the apparatus in accordance with the present invention is the application software for controlling the computer 101. The application software may be provided in any suitable software language which is compatible with the operating system of the computer 101. Preferably, the software for use with the apparatus in accordance with the present invention comprises customised "vision block" software of the kind which is readily available commercially.

The application software comprises an internal database or instructions for querying an external database. The database forms an integral part of the apparatus described herein for determining one or more physical properties of a cigarette. In particular, the database is adapted to store nominal values for each of a number of physical properties of interest for one or more different brands of cigarettes. Thus, for each of the one or more cigarette brands, the database comprises nominal values for the following physical properties:

| | |
|---|---|
| Total length | $N_l$ |
| Filter section length | $N_{l_f}$ |
| Tipping length (overwrap) | $N_{O_w}$ |
| Over-lap | $NO_l$ |
| Diameter | $N_d$ |

In addition the database may store nominal values for the axial positions of other visible external features of the cigarette 10 with respect to a notional reference end of the cigarette, such as said printed matter on the cigarette paper 20 with respect to the first end 25 of the filter section 14, and the axial thickness and separation of said bands 32. The database may also comprise contrast maps for typical, representative regions of the tobacco column 12 and filter section 14 as described in more detail below.

Since CCD based cameras generally suffer from blooming, it is important to ensure that at no point does the image become overexposed. Cigarette papers and filter rods vary considerably in colour and albedo values. Furthermore two products which appear to be very similar one to the other to the human eye, may actually appear to be substantially different from each other to the camera 222 under infrared light. The determination of optimum shutter speeds is therefore carried out empirically on actual product samples, and the values obtained for a given brand are stored in the database. For each brand, three different shutter speeds are typically required: a first relatively slow shutter speed for detecting the position of the internal end face 27 of the filter rod under intense illumination by said back-light 252; a second relatively fast shutter speed for detecting bright spots corresponding to voids in the cigarette 10, e.g. between the tobacco column 12 and filter section 14, under illumination from said back-light 252; and a third intermediate shutter speed for detecting edges of the cigarette 10 in the image under diffuse light from said side-lights 254 against said dark background. Said first low shutter speed is needed so that as much light as possible is able to penetrate the filter section 14. This may lead to some overexposure of the image, but the inaccuracies caused by any apparent blooming of the image are expected to lie within required tolerances for this measurement; vertical smearing is not significant due to the projection technique used to locate edges within an image.

The apparatus in accordance with the present invention may be supplied with a database pre-programmed with the above information relating to a range of well known cigarette brands, although the application software/database is configured to allow an operator to input corresponding data relating to additional cigarette brands if required.

The software may have a modular or integrated architecture. However, the software is required to carry out a number of distinct functions as follows:

Autofocus

Said infra-red digital video-camera 222, as described above, is adapted to image cigarette or other rolled smoking article or filter rod disposed within the field of view in the object space 250 between the upper portion 234 of the bracket 230 and the jig member 240. The focal length of the digital infra-red camera can be adjusted by operating the camera's auto-focussing device as described above.

Accuracy of the apparatus in accordance with the present invention for the measurement of diameter in particular depends upon the camera 222 being focussed on the central axis 16 of the cigarette, so that the lateral edges of the cigarette in the image are sharply focussed. Since the cigarette is supported on said rollers 310-313 during the vision inspection cycle, said axis 16 is further away from the camera 222 for large diameter products than it is for a small diameter ones.

Accordingly the application software comprises a selectively operable focussing routine which comprises serially sampling the image of a reference object placed in said object space 250 to obtain serial samples whilst the auto-focussing motor is operated to change the focal length step-wise from one extreme ($f_1$) to the other extreme ($f_N$), the reference object being shaped and dimensioned to have at least one sharp edge within the camera's field of view. In preferred embodiments, the sampling rate of the frame grabber is synchronised to operation of the auto-focussing motor (or vice versa), so that one sample is taken for each position of the auto-focussing motor. Said serial samples are then processed by said application software using image processing techniques of the kind referred to above to detect said edge and to determine in which sample the edge is sharpest, and thus in focus. Since it is unlikely that an exact figure will be achieved, a sharpness tolerance is applied. Were the sharpness to be plotted against focal distance, a Gaussian distribution curve would be apparent The auto-focussing motor is then operated under the control of the application software to return the auto-focussing device to the focal length corresponding to that sample such that the camera 222 is focussed. As the motor does not stop immediately, the edges should be slightly sharper when the motor does finally stop.

Preferably the reference object has substantially the same shape and dimensions within the field of view as a cigarette, filter rod, or other rolled smoking article to be tested. In particular the reference object may comprise a rod having substantially the same size and shape as the cigarette or filter rod, and made from a dimensionally stable material.

Calibration

The application software further comprises a calibration component which is adapted to relate distances in the image measured in pixels to actual distances in the field of view, typically in millimeters. The ratio of pixels to millimeters depends on the optical properties of the camera 222 and on the optical distance between the object and the lens portion 224 of the camera 222. A conversion factor for converting pixels distances into actual distances may be pre-programmed into the application software, or the application software may provide a utility for recalculating and storing the conversion factor by imaging a reference object of known dimensions in the field of view. Said reference object may have substantially the same shape and dimensions in the field of view as the rolled smoking article or filter rod to be tested, and in particular may comprise a substantially cylindrical rod made of a dimensionally stable material. In some embodiments, the same reference object may be used for calibration and auto-focussing as described above.

Figure 6:
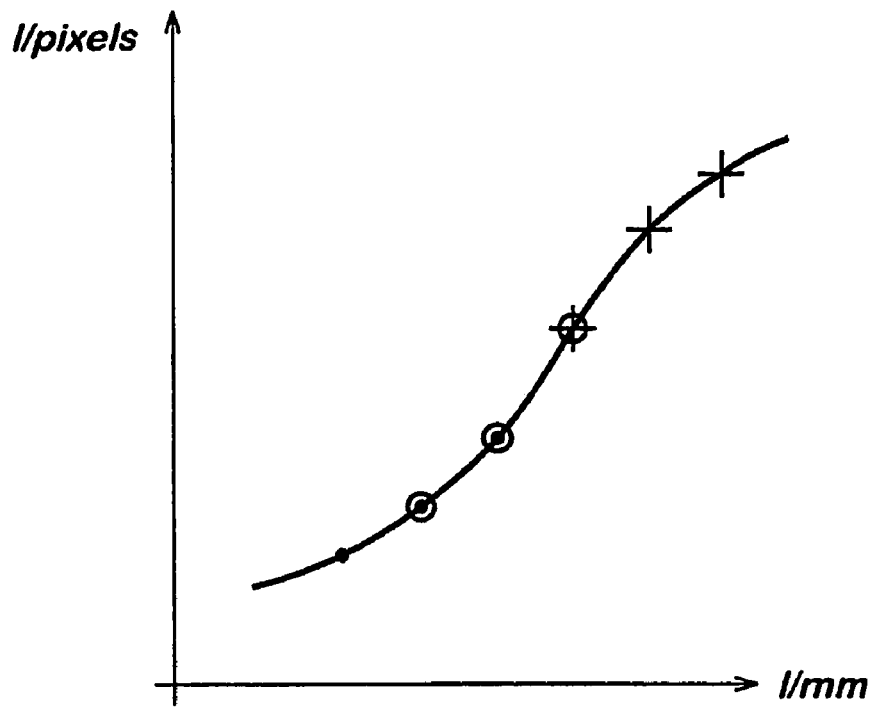
FIG. 6 is a graph which shows an illustrative, non-linear relationship between pixels and actual distance for a digital camera.

It has been found that the measurement of diameter in accordance with the present invention is particularly sensitive to optical effects associated with the vision system 200. FIG. 6 shows a typical calibration curve of actual length versus pixels. It will be noted that the curve is non-linear. Accordingly it is desirable to calibrate the vision system 200 at least at two different known diameters on either side of the nominal diameter ($N_d$) of a cigarette 10 or other rolled smoking article or filter rod to be tested, and then to interpolate between those known diameters to establish a calibrated scale for the vision system 200. A plurality of reference rods of different, accurately known diameters may be used. Preferably three different reference rods are used to give three calibration points across a range of diameters corresponding to the nominal diameter of the rolled smoking article or filter rod to be tested: one rod at each end of the range and one towards the middle of the range. As shown in FIG. 6, five different reference rods can be used to give three different calibration ranges, each range being calibrated at three known calibration points. In FIG. 6, the calibration points in each range are represented respectively by the symbols •, ○ and +.

Establishment of a Datum Position

Upon powering up the apparatus in accordance with the invention, the application software is adapted to cause appropriate control signals to be transmitted by the motion controller 106 to the servo motor of the transport system 300 for moving the end face 329 of the pusher portion 328 into the field of view of the camera 222. During the establishment of a datum position, the application software causes appropriate control signals to be sent to the power control box 255 of the vision system 200 via the frame-grabber 104 for activating the side-lights 254 for illuminating the field of view with diffuse light. The image of the pusher portion 328 is sampled by the frame-grabber 104 and processed by the application software until the end face 329 of the pusher portion 328 is detected in the field of view. The servo motor is then halted and its position stored as a datum position. Once the datum position of the pusher portion 328 has been established, the servo motor is operated in reverse to return the pusher portion 328 to a home position as shown in FIG. 3, ready to receive a cigarette for analysis.

Determine Brand and Orientation of Cigarette

In use, the apparatus according to the present invention is adapted to receive serial cigarettes to be analysed from a maker. As mentioned above, the nominal physical properties of cigarettes vary from brand to brand, and the orientation of the cigarette (i.e. tobacco column 12 or filter section 14 first) varies from maker to maker and from line to line within a maker. The application software in accordance with the present invention allows the operator to input data concerning the brand and orientation of cigarettes to be tested. Upon input of that data, the software is adapted to look-up the nominal physical properties of the cigarettes to be tested in said database.

Measurement of Actual Length (l)

Figure 7:
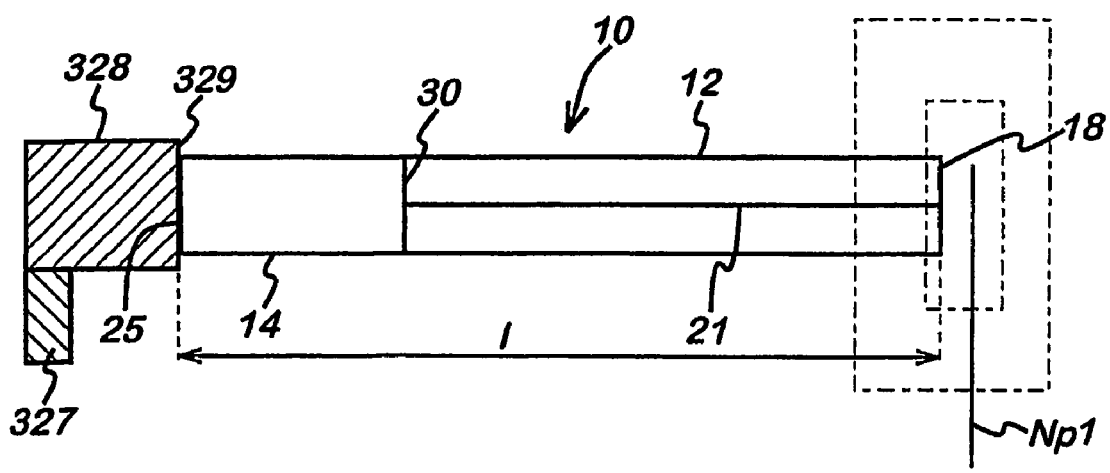
FIG. 7 is a schematic diagram showing the measurement of the overall length of a cigarette in accordance with the present invention.

With reference to FIG. 7, the application software is adapted to determine the actual length (l) of a cigarette 10 as follows. Based on the nominal length ($N_l$) of the cigarette, the application software calculates a first position of the pusher portion 328 corresponding to the nominal length such that with one end 18, 25 of the cigarette 10 in abutment with the end face 329 of the pusher portion 328, the other end 25, 18 is disposed within the field of view of the camera 222. The application software also determines a first nominal position ($N_{p1}$) within the field of view corresponding to said nominal length ($N_l$) which is the nominal position of said other end 25, 18 of the cigarette 10 if the cigarette 10 is of the nominal length ($N_l$). The application software also defines a first region of interest 401 around the first nominal position ($N_{p1}$) which region of interest 401 encompasses all likely actual positions of the other end 25, 18 of the cigarette 10 when the one end 18, 25 is disposed at the first pusher position, based on the statistical deviation of the actual length (l) of the cigarette 10 from the nominal length ($N_l$).

The application software further comprises instructions for them transmitting appropriate control signals via the motion controller 106 to the servo motor for moving the pusher portion 328 to said first position. The pusher portion 328 is halted at said first position as shown in FIG. 7 in which said other end 25, 18 of the cigarette 10 is disposed within the region of interest 401 in the field of view of the camera 222. The computer 101, in accordance with the instructions encoded in the application software, then causes the frame-grabber 104 to transmit appropriate instructions to the vision system 200 for actuating the side-lights 254 for illuminating with diffuse light the field of view in said object space 250. The other end 25,18 of the cigarette 10 within the region of interest is imaged by the camera 222, and the image is sampled by the frame-grabber 104 at said third intermediate shutter speed. The image sample is then processed by the computer 101 to detect the position of the other end 25, 18 of the cigarette 10 and to determine its position relative to the nominal position ($N_{p1}$). The difference ($\delta_l$) between the actual position of the other end 25,18 and the nominal position ($N_{p1}$) is then added or subtracted (depending on whether $\delta_l$ is positive or negative) from the nominal length ($N_l$) as appropriate to derive the actual length (l) of cigarette 10.

$$l = N_l + \delta_l$$

In FIG. 7, the cigarette 10 is shown tobacco column 12 first, although as mentioned above, the cigarette 10 may be conveyed on the transport system 200 either tobacco column 12 first or filter section 14 first. However, for the purposes of measuring the total length (l) of cigarette 10, the orientation of the cigarette 10 is immaterial.

Determination of Axial Positions and Measurement of Lengths Dependent on Cigarette Orientation In addition to the total length (l) of the cigarette 10, the apparatus in accordance with the present invention is advantageously adapted to determine the axial positions of one or more internal or external features with respect to a notional reference end 18, 25 of the cigarette, such for example as the position of the one end face 27 of the filter section 12 relative to the first end 25, which corresponds to the length of the filter section 14 ($l_f$), and the position of said edge 30 relative to said first end 25, which corresponds to the axial length ('overwrap") of the tipping paper 28 ($O_w$).

Figure 8:
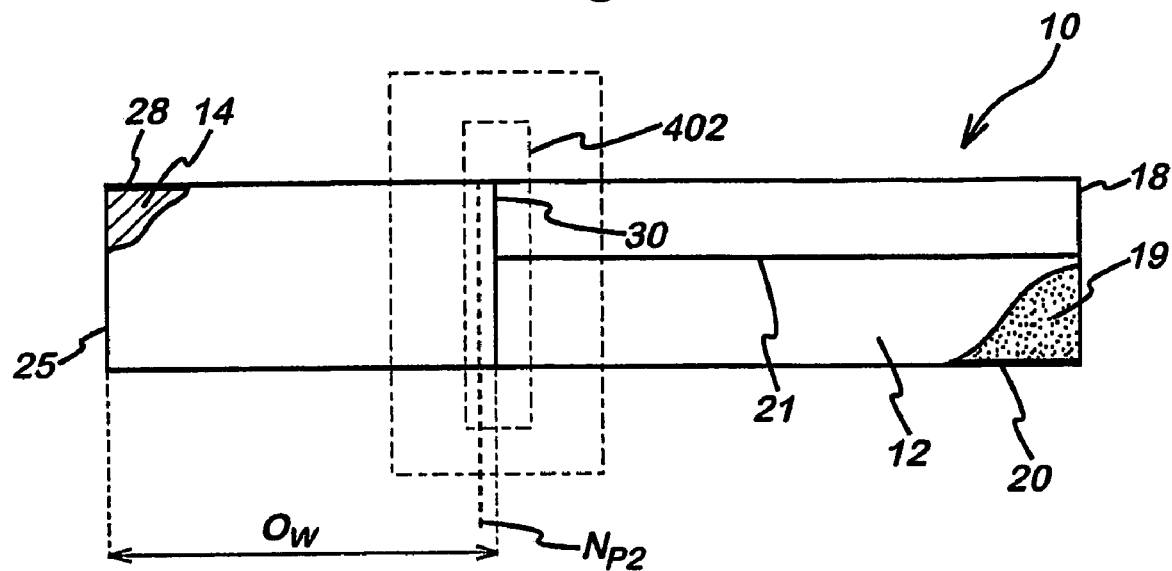
FIG. 8 is a schematic diagram showing the measurement of the length of a tipping layer of a cigarette in accordance with the present invention.

In order to measure the overwrap ($O_w$), the application software first determines the orientation of the cigarette 10 from the user-inputted data. The software then looks up in said database the nominal length ($N_{O_w}$) of the tipping paper 28 and calculates a second position of pusher portion 328 relative to the datum position such that when the pusher portion 328 is disposed at said second position, the edge 30 of the tipping paper 28 is disposed within the field of view. The application software also calculates a nominal position ($N_{p2}$) for said edge 30 and a region of interest 402 to be imaged for detecting the actual position of said edge 30 as shown in FIG. 8.

The application software comprises instructions for then transmitting appropriate control signals to the transport system 300 via the motion controller 106 for moving the pusher portion 328 to the second position such that the edge 30 of the tipping paper 28 is disposed in the field of view. The sidelights 254 are then actuated, illuminating the cigarette 10 within the field of view, and the digital image of the cigarette 10 obtained by the camera 222 is sampled by the frame-grabber 104 and processed by the computer 101 in accordance with the software to determine the actual position of the edge 30. The difference ($\delta_{O_w}$) between the actual position of the edge 30 and its pre-calculated nominal position ($N_{p2}$) is calculated and, depending on the orientation of the cigarette 10 in the transport system 300, said difference is applied to the nominal length ($N_{O_w}$) of the tipping paper in order to calculate the actual length of the tipping paper ($O_w$).

$$O_w = N_{O_w} + \delta_{O_w}$$

Where the cigarette 10 is conveyed in the transport system 300 tobacco column 12 first, such that the filter section 14 abuts the end face 329 of the pusher portion 328, the axial length ($O_w$) of the tipping paper 28 is equal to the distance between the second position of the pusher portion 328 and the detected actual position of the edge 30 of the tipping paper 28. Where the cigarette 10 is conveyed in the opposite direction, i.e. tipping section 14 first, with the tobacco column 12 abutting the end face 329 of the pusher portion 328, then the length of the tipping paper 328 can be calculated from the actual length (l) of the cigarette 10, determined as described above, minus a first nominal distance between the second pusher position and the nominal position ($N_{p2}$) of said edge 30, adjusted by the difference ($\delta_{O_w}$) between the nominal position ($N_{p2}$) and the actual position of the edge 30.

Figure 9:
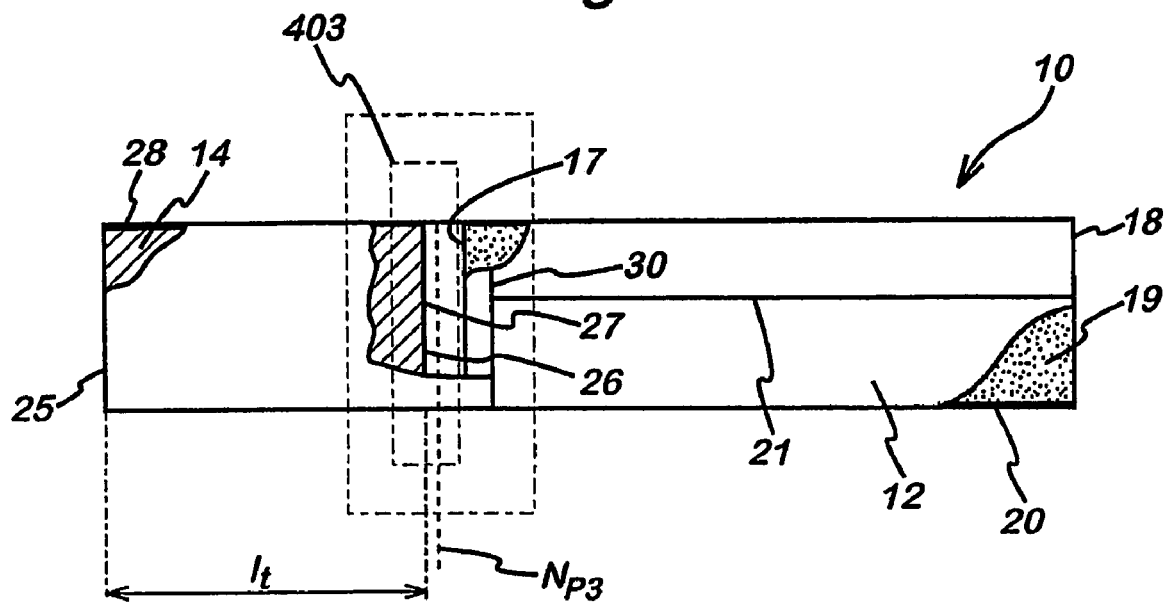
FIG. 9 is a schematic diagram showing the measurement of the length of a filter section of a cigarette in accordance with the present invention.

With reference to FIG. 9, the internal length ($l_f$) of the filter section 14 can be determined in accordance with the present invention in a manner similar to the determination of the overwrap ($O_w$) of the tipping paper 28. The application software first determines the orientation of the cigarette 10 in the transport system 300 and looks up in the database the nominal length ($N_{l_f}$) of the filter section 14. Based on the orientation of the cigarette and the nominal length ($N_l$), the application software calculates a third position for the pusher portion 328 at which the one end face 27 of the filter section 14 is disposed in the field of view. The application software also calculates a third nominal position ($N_{p3}$) for said end face 27 based on the nominal length of the filter section 14 and the orientation of the cigarette 10.

The application software contains instructions for operating the servo motor to move the pusher portion 328 to the third position as shown in FIG. 9 such that the one end face 27 is positioned in the vicinity of the third nominal position ($N_{p3}$) within a third region of interest 403 calculated by the software on the basis of the statistical deviation of the actual length of the filter section 14 from its nominal length ($N_{l_f}$). The application software contains instructions for actuating the backlight 252 mounted on the upper portion 234 of the bracket 230 which is of sufficient luminosity that infra-red light is transmitted through the body of the cigarette 10. Owing to the properties of the filter rod 14, the one end face 27 at the interface between the tobacco column 12 and filter section 14 shows up in the image of the cigarette in the field of view as a bright shape. The computer 101 processes a sample of the image obtained at said first slow shutter speed and captured by the frame-grabber 104 to locate the one end face 27 in the region of interest 403 and to calculate the difference between the actual position of the end face 27 and the nominal position ($N_{p3}$). As described above, the actual length ($l_f$) of the filter section 14 can then be calculated from its nominal length ($N_{l_f}$) and the difference ($\delta_{l_f}$) between the third nominal position ($N_{p3}$) and the actual position of the end face 27 and, depending on the orientation of the cigarette 10, the total length (l) of the cigarette 10.

$$l_f = N_{l_f} + \delta_{l_f}$$

In addition, the over-lap length ($O_l$) can be calculated by the software as the difference between the actual axial length of the tipping paper ($O_w$) and the actual length ($l_f$) of the filter section 14.

The technique described can be also used to determine the axial position of any visible internal or external feature of the cigarette 10 relative to a notional reference end 18, 25 of the cigarette. For example, as mentioned above, the outer surface of many cigarettes is over-printed with alpha-numeric characters or graphic devices, which are usually indicative of the brand or kind of cigarette. FIG. 1B, referred to above, shows representative over-printing on the outer surface of the cigarette paper 20 which comprises the representative word "BRANDING". As shown in FIG. 1B, the word "BRANDING" is aligned circumferentially with respect to the longitudinal axis 16 of the cigarette 10 and is positioned in juxtaposition with the edge 30 of the tipping paper 28. For quality control purposes, it is desirable that the over-printing should be accurately and consistently positioned on the cigarette, and accordingly the position of the over-printing is typically specified with reference to one end 18, 25 of the cigarette 10, typically the first end 25 of the filter section 14, which is usually guillotined accurately during manufacture of the cigarette 10. In order to specify the axial position of such over-printing, the axial position of one or more predefined points of the over-printing may be specified. An advantage of specifying two or more such points which are circumferentially spaced with reference to the axis 16 of the cigarette 10 is to ensure that the over-printing is also properly aligned circumferentially. For example, in the case of the word "BRANDING", printed on the cigarette as shown in FIG. 1B, it is desirable to ensure that the word is not skewed with respect to said longitudinal axis. Thus the axial position of the word "BRANDING" may, by way of example, be specified by defining the axial positions of a plurality of predefined points of respective different letters of the word. For example, the axial position of the upper extremity of the letter "B" may be specified with reference to the first end 25 of the filter section 14, and the upper extremity of the letter "G" (not shown) may also be specified with reference to the first end 25 as a notional reference end.

The actual axial position of the or each defined point of a visible feature such, for example, as the word "BRANDING" as shown in FIG. 1B, is then determined by the application software as described above by first calculating a corresponding position for the pusher portion 328 relative to the datum position such that when the pusher portion is disposed at the corresponding position, the defined point is disposed within the field of view in proximity to a corresponding nominal position for the defined point within a corresponding region of interest to be imaged for detecting the actual position of the defined point, the corresponding nominal position and corresponding region of interest also being calculated by the application software on the basis of the nominal, specified position for the point of the visible feature relative to one end 18, 25 of the cigarette.

The application software comprises instructions for then transmitting appropriate control signals to the transport system 300 via the motion controller 106 for moving the pusher portion 328 to the corresponding position, such that said defined point is disposed within the field of view. The side lights 254 or back-light 252 are then actuated, depending on whether the visible feature is external or internal to the cigarette 10, such that the visible feature is conspicuous in the field of view, and the shutter speed of the camera 222 is adjusted accordingly. In the case of over-printed characters such, for example, as the word "BRANDING" as shown in FIG. 1B, the different colour or tone of the ink used for the over-printing as compared with the background colour of the cigarette paper 20 means that the over-printing is conspicuous by dint of its significant contrast with the background.

As described above, the image of the cigarette 10 within the field of view is then sampled by the frame grabber 104 and processed by the computer 101 in accordance with the application software to locate the defined point of the feature in the corresponding region of interest, and to calculate the axial difference between the actual position of the defined point of the feature and its corresponding nominal position. The actual axial position of the defined point with respect to the reference end 18, 25 of the cigarette 10 is then calculated by applying the difference between the actual and corresponding nominal positions of the defined point of the feature to the corresponding nominal position of the defined point with respect to the reference end.

Where two or more defined points of a visible feature are to be located, the application software may then cause the transport system 300 to move the pusher portion 328 to another position corresponding to the next defined point of the feature. However, where two or more defined points of a feature are axially closely spaced or substantially axially aligned, then such defined points of the feature may be visible within the field of view of the camera 222 with the pusher portion 328 disposed at a single position. Where the defined points of a feature are circumferentially spaced, then it may be necessary, with the pusher portion stationary, to rotate the cigarette 10 about its axis 16 to image the defined points by operating the rollers 310-313 of the transport system 300 as described above.

Other Axial Measurements

In addition to visible features which are positioned with reference to a notional reference end 18, 25 of the cigarette, the cigarette may also comprise one or more visible, external patterns which are not positioned with respect to such a reference end, but consist of a regularly repeating design, said design comprising one or more features which are visible by contrast with immediately adjacent portions of the outer surface of the cigarettes 10. As mentioned above, said cigarette paper 20 may comprise a plurality of regularly axially spaced, circumferential, relatively dark bands 32 of prescribed thickness and spacing. As described above, the database may store nominal values for the axial thickness and separation of such bands 32, and the application software may comprise a sub-routine as described below for processing an image of an appropriate portion of the outer surface of the cigarette 10 for measuring the axial thickness and spacing of the bands 32. Associated with the nominal thickness and spacing of the bands 32, the database may comprise a nominal position for the pusher portion 328 of the transport system 300 such that the, cigarette 10 is positioned with respect to the datum position with a representative portion of the outer surface of the cigarette 10 is disposed within the field of view to allow the bands 32 to be imaged. The application software in accordance with the sub-routine thus causes the transport system 300 to move the pusher portion 328 to said nominal position, and the image of the cigarette 10 is then sampled by the frame grabber 104 and processed by the application software to detect, in accordance with the image processing techniques referred to above, the opposite edges 33, 34 of two adjacent bands 32 as shown in FIG. 1A. The axial thickness of the bands 32 can then be calculated by determining the axial distance between the opposite edges 33, 34 of one band 32, and the axial spacing, or pitch, of the bands 32 can be calculated by determining the axial distance between one edge 33, 34 of one band 32 and the corresponding edge 33, 34 of the adjacent band 32. The actual measured thickness and spacing of the bands 32 is then compared by the application software to the nominal values of those physical properties in the database, and the application software may trigger a suitable software or hardware alarm if the actual spacing and/or thickness of the bands 32 are significantly different from the stored nominal values, indicating that the wrong paper 20 has been used in the manufacture of cigarette 10.

Rotational Measurements

In addition to measurements of length, the apparatus in accordance with the present invention is also adapted to determine one or more physical properties of the cigarette 10 which relate to the diameter (d) of the cigarette. Owing to the orientation of the camera 222 with respect to the cigarette 10 such measurements of diameter can be made taking advantage of the maximum resolution of the camera. The application software can also determine the respective directions of wrapping of the cigarette paper 20 and tipping paper 28 (and thereby identify the particular line on a maker on which a cigarette was made). The diameter (d) of the cigarette 10 can be measured at any number of points along its axial length, but in the embodiment described, the diameter (d) is measured at two spaced points along the length of the cigarette, namely at one point on the tobacco column 12 of the cigarette and at another point on the filter section 14.

The application software first determines the orientation of the cigarette 10 from the user-inputted data. The software then looks up the nominal diameter ($N_d$) of the cigarette 10 in the database according to its brand. The application software also calculates fourth and fifth positions for the pusher portion 328 of the transport system 300 for moving the cigarette to respective positions such that the points at which the diameter (d) is desired to be measured are disposed in the field of the view.

Figure 10:
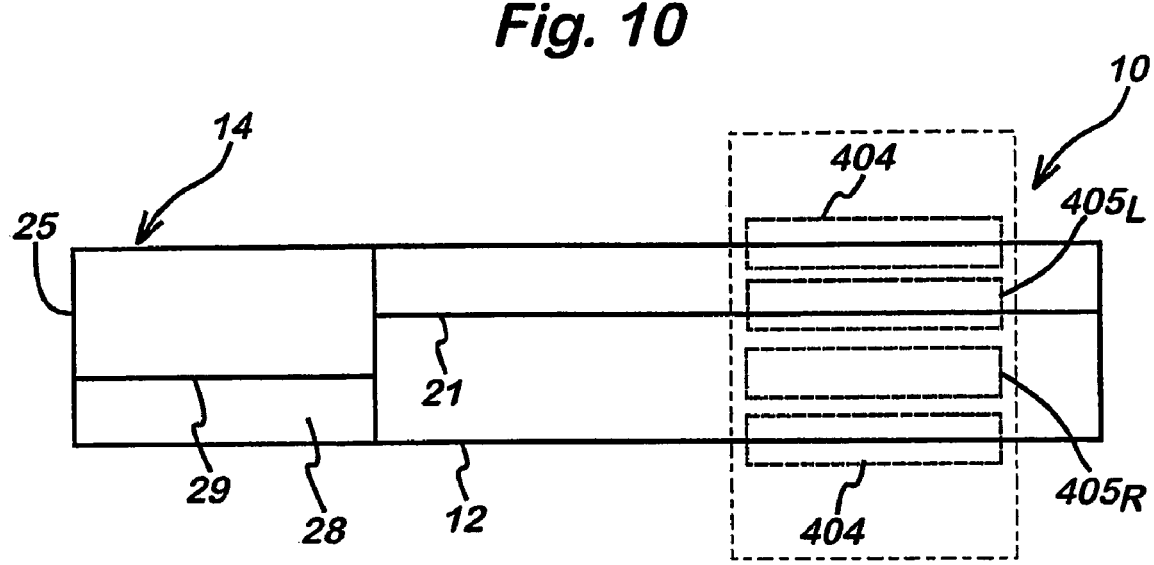
FIG. 10 is a schematic diagram showing the determination of the direction of wrapping of a circumferentially wrapped outer layer of a cigarette in accordance with the present invention and the measurement of the diameter of the cigarette.

The software defines two inner and two outer laterally spaced regions of interest as shown in FIG. 10. The two laterally spaced outer regions of interest 404 are derived from the nominal diameter ($N_d$) of the cigarette 10 and encompass all statistically likely positions of the opposite lateral edges of the cigarette 10 when viewed in profile in the field of view. The purpose of the two inner laterally spaced regions of interest $405_L$ and $405_R$ is now be described.

As described above, each of the cigarette and tipping papers 20, 28 is wrapped circumferentially about its respective section 12, 14 of the cigarette 10 to overlap itself and to form a respective longitudinal seam 21, 29. Since the cigarette 10 is directional (asymmetrical), each of the cigarette and tipping papers 20, 28 may be wrapped independently clockwise or counter-clockwise about the cigarette 10 relative to its direction The infra-red side-lights 254 are positioned within the object space 250 of the vision system 200 to illuminate obliquely the cigarette 10 within the field of view of the camera 222 to enhance the shadows cast by the seams 21, 29. The visibility of each seam 21, 29 within the field of view depends on the rotational orientation of the cigarette 10 about its longitudinal axis 16.

As described above, the transport system 300 includes two pairs of juxtaposed rollers 310-313 for rotating the cigarette 10 about its axis in the field of view. Owing to the handed nature of each seam 21, 29, the shadow cast by the seam 21, 29 will appear in only one of the inner regions of interest $405_L$, $405_R$ as the cigarette 10 rotates about its axis, depending on the direction of wrapping of the respective paper 20, 28. Thus, the direction of wrapping of the cigarette and tipping papers 20, 28 can be ascertained in accordance with the present invention by rotating the cigarette 10 about its axis in the field of view of the camera 222 and determining in which of the two inner regions of interest $405_L$, $405_R$ the shadow cast by the seam 21, 29 appears.

The application software thus encodes instructions for the transport system 300 to move the cigarette 10 to the fourth position such that one of the tobacco column 12 or filter section 14 is disposed in the field of view. The application software then switches on the digital output card 107 so as to cause the rollers 310-313 to rotate the cigarette 10 about its axis 16 at a substantially constant speed of rotation. The side-lights 254 are switched on to illuminate obliquely the part of the cigarette 10 within the field of view, thus accentuating the shadow cast by the seam 21, 29. The image produced by the camera 222 at said third intermediate shutter speed is repeatedly sampled by the frame-grabber 104, and each sample is processed within the inner regions of interest $405_L$, $405_R$ to detect the position of the shadow cast by the seam 21, 29. As mentioned above, the direction of wrapping of the cigarette paper 20 or filter paper 28 is determined by the inner region of interest $405_L$, $405_R$ in which the shadow appears.

The appearance of the shadow cast by the seam 21, 29 in one of the inner regions of interest $405_L$, $405_R$ also provides a convenient circumferential marker on the cigarette 10 for the start of a complete rotation of the cigarette 10 about its axis 16. The application software thus causes the digital card 107 to continue to transmit an 'on' signal such that rollers 310-313 continue to rotate the cigarette 10 about its axis 16 until the shadow reappears in the same inner region of interest $405_L$, $405_R$, indicating that the cigarette 10 has completed a complete 360° rotation about its axis 16, whereafter the computer 101 causes the digital card 107 to switch off.

During the complete rotation of the cigarette 10, the image samples obtained by the frame-grabber 104 are processed to detect in the outer regions of interest 404 the positions of the lateral edges of the profile of the cigarette. In each sample, the distance ($d_n$) between the edges is calculated to obtain a measurement of diameter for that image sample.

The mean diameter ($d_{mean}$) is calculated by calculating the average diameter of all the image samples in a complete rotation of the cigarette 10 about its axis 16.

$$d_{mean} = \text{average}(d_n)$$

The mean circumference ($c_{mean}$) of the cigarette 10 can be calculated from the mean diameter.

In addition, a number of other physical properties of the cigarette 10 can be obtained as follows.

Figure 11:
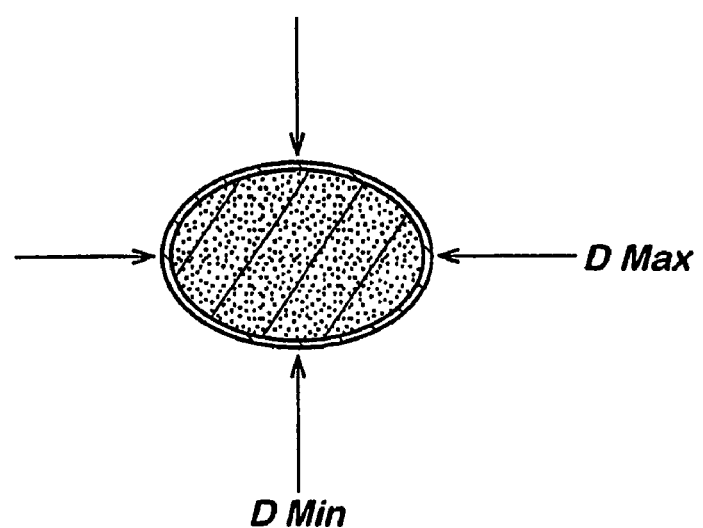
FIG. 11 is a schematic cross-sectional view of a cigarette showing the maximum and minimum diameters of the cigarette.

With reference to FIG. 11, the maximum and minimum diameter of the cigarette 10 at the fourth position can be obtained ($d_{max}$, $d_{min}$) the ovality of the cigarette is defined by $d_{max}$ minus $d_{min}$.

$$\text{Ovality} = d_{max} - d_{min}$$

The shape of the cigarette is defined as standard deviation of the diameter of the cigarette 10 as measured in all of the image samples obtained during a complete revolution of cigarette 10 about its axis 16

$$\text{Shape} = \sigma(d_n)$$

The roundness of the cigarette 10 can be calculated in accordance with the equation:

$$\text{Roundness} = [1 - (\text{ovality}/d_{mean}) \times 100]$$

Once all the diameter measurements have been made at one of the two points with the pusher portion 328 in the fourth position, the application software then causes the motion controller 106 to send appropriate control signals to the transport system 300 for moving the cigarette to the fifth position, so that the procedure described above can be repeated to measure serially the diameter ($d_n$) of the cigarette 10 at the other of the two positions in a plurality of image samples as the cigarette 10 rotates through a complete revolution about its axis 16 and to determine the direction of wrapping of the tipping paper 28 or cigarette paper 12 at the other point Knowledge of the respective directions of wrapping of the cigarette and tipping papers 20, 28 can be used to identify the particular line on a maker on which the cigarette 10 was made.

Detection of Defects

The apparatus in accordance with the present invention is adapted to detect the presence of defects in a cigarette 10, such as a void between the tobacco column 12 and the filter section 14 as shown in FIG. 9. In order to detect such a void, the application software determines the orientation of the cigarette 10 from the user-inputted data and looks up in the database the nominal length ($N_{lf}$) of the filter section 14. The application software then calculates a sixth position of the pusher portion 328 (which may be the same as the third position). The application software then causes the motion controller 106 to transmit appropriate control signals to the transport system 300 for moving the pusher portion 328 to the sixth position such that the interface between the tobacco column 12 and filter section 14 is disposed in the field of view in the test space 250. When the pusher portion is in the sixth position, the application software causes the frame-grabber 104 to transmit appropriate control signals to the power block 255 of the vision system 200 for switching on the infra-red back-light 252. The intensity of infra-red light transmitted by the cigarette 10 depends on a number of factors, including the density and thickness of the cigarette and on the material from which the cigarette is manufactured. An unwanted void between the tobacco column 12 and filter section 14 shows up in the image obtained by the camera 222 as an area of extraordinary brightness. Since the back-light is able to penetrate easily the cigarette paper 20 and, when detecting voids between the cigarette column 12 and filter section 14, the cigarette paper 20 and tipping paper 28, said second relatively fast shutter speed can be used. The application software is configured to detect such areas of unusual brightness and to indicate the presence of an internal void where such an area of unusual brightness is detected. Similarly, the application software can be configured to detect voids at the opposite ends 18, 25 of the tobacco column 12 and filter section 14 respectively.

As mentioned above, in addition to intended visible features (internal or external) the cigarette 10 may also comprise one or more unintended or undesirable, external visible features such as ventilation holes and/or spot marks. Such unintended features may be conspicuous in an image of the cigarette 10 as one or more discreet dark areas in contrast to the surrounding areas of the outer surface of the cigarette 10 and may appear at random positions.

The cigarette 10 comprises a plurality of different regions, generally indicated by A and B in FIG. 1. The cigarette 10 in FIG. 1 comprises two different regions A, B. One region A corresponds to the cigarette paper 20 which is wrapped around the tobacco column 12, and the other region B corresponds to the tipping paper 28 that is wrapped around the filter section 14 and the interface between the tobacco column 12 and filter section 14. Each region A, B has a different, respective normal background pattern. For example, the cigarette paper 20 in region A may be generally featureless or may comprise circumferential bands 32 of the kind described above. The region B may also be generally plain, or may comprise a speckled pattern which is characteristic of tipping papers. The tone of region B, in a typical cigarette, is darker than the tone of region A.

For each region A, B, the database incorporated in the application software, or accessible by the application software, stores a corresponding reference contrast map comprising a nominal image of a representative portion of the region. Thus, for each region, the reference contrast map may comprise a two dimensional map of contrast for a representative portion of the region, i.e. a discreet area which is generally smaller than the whole region A, B and which may form a repeat pattern for the whole region A, B. Associated with each reference contrast map, the database may further comprise nominal axial positions for the boundaries of the region A, B with respect to a reference end 18, 25 of the cigarette 10. Based on the nominal boundary positions, the application software may calculate, depending on the orientation of the cigarette 10 in the transport system 300, corresponding positions for the pusher portion 328 at which the boundary between two adjacent regions A, B of the cigarette 10 is disposed within the field of view of the camera 222.

The application software may be adapted to drive the transport system 300 for moving the pusher portion 328 step-wise such that the cigarette 10 is moved axially by integer steps through the field of view. At each integer position, the application software may operate the transport system 300 to rotate cigarette 10 on the rollers 310-313 whilst the pusher portion 328 is stationary. As the cigarette 10 is rotated at each integer position, the image of the cigarette 10 within the field of view is sampled by the frame grabber 104, and each image sample is processed to generate a two dimensional contrast map of the portion of the cigarette 10 within the field of view. Said contrast map effectively comprises a two dimensional map of the variations in contrast of the portion of the cigarette 10 within the field of view. The contrast map for each sample is then compared by the application software with the corresponding reference contrast map, and any unexpected differences between the contrast map and reference contrast map are detected. When the cigarette 10 is moved axially to a nominal position corresponding to a boundary between two adjacent regions A, B as described above, the application software swaps the active reference contrast map for another reference contrast map corresponding to the next succeeding region A, B of the cigarette 10 to be imaged.

The application software may be configured to trigger a suitable alarm in the event that more than a predetermined number of significant differences between a contrast map and its corresponding reference contrast map are detected, indicating that the external surface of the cigarette 10 comprises more than a predetermined threshold quantity of unwanted, external visible features such as spot marks or ventilation holes.

The apparatus in accordance with the present invention as hereinbefore described is thus able to determine automatically a plurality of physical properties of a cigarette 10 including the total length (l) of the cigarette, the length ($l_f$) of the filter section, the length of the over wrap ($O_w$) and overlap ($O_l$), and the average diameter ($d_{mean}$) and circumference ($c_{mean}$) of the cigarette 10. By rotating the cigarette 10 about its axis, the respective positions of the longitudinal seams 21, 29 of the cigarette and tipping papers 20, 28 can be detected to determine the respective, independent directions of wrapping of those papers 20, 28 relative to the axial direction of the cigarette 10. In addition, the positions of the seams 21, 29 provide convenient markers for the circumferential/rotational position of the cigarette allowing the diameter ($d_n$) of the cigarette to be sampled as it is rotated through a complete 360° revolution. By obtaining multiple samples of the image of the cigarette as it rotates, the application software in accordance with the present invention is able to calculate the maximum and minimum diameters ($d_{max}$ and $d_{min}$) of the cigarette and, from those figures, to calculate a number of other properties such as shape, roundness and ovality. Furthermore, the apparatus in accordance with the present invention can detect unwanted voids in the cigarettes by illuminating the cigarette within the field of view with an intense back-light 252 and detecting areas of unusual brightness in the image.

For measurements of length, the apparatus according to the invention has a resolution of about 0.1 mm, an accuracy of about ±0.5 mm, a repeatability of about ±0.3 mm and a reproducibility of about ±0.5 mm. For diameter measurements, the apparatus of the present invention has a resolution of about 0.01 mm, an accuracy of about ±0.01 mm, a repeatability of about ±0.02 mm and a reproducibility of about ±0.03 mm.

A significant advantage of the apparatus according to the present invention is that one cigarette 10 can be analysed every approximately ten seconds. By sampling cigarettes from a mass flow of cigarettes emerging from a maker and measuring the physical properties of the sampled cigarettes at a rate of one every ten seconds, the variation in the physical properties of the cigarettes from the maker with time can be visualised. As mentioned above, in many modern makers, cigarettes are made in two parallel streams which are then merged for packaging. The detection of the respective directions of wrapping of the cigarette and tipping papers 20, 28 allows each cigarette to be identified with a particular line of the maker.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. An apparatus for determining one or more physical properties of a rolled smoking article or filter rod, said rolled smoking article or filter rod having a longitudinal axis, said apparatus comprising:
   an imaging device defining a field of view disposed along an optical axis, said imaging device imaging a rolled smoking article or filter rod in said field of view;
   a positioning unit which positions a smoking article or filter rod in said field of view such that the longitudinal axis of the smoking article or filter rod is substantially orthogonal to the optical axis of the imaging device;
   an illuminating unit which illuminates said field of view;
   a rotating mechanism which rotates said smoking article or filter rod about its longitudinal axis in said field of view;
   a processor which processes said image to determine one or more physical properties of a smoking article or filter rod in said field of view; and
   a control unit which controls said processor, said control unit comprising a database, which database is constructed and arranged to store a predetermined nominal diameter of said rolled smoking article or filter rod, said control unit defining two laterally spaced regions of interest of said field of view corresponding to the nominal width, each of which regions of interest encompasses all likely positions of a respective one of the opposite edges, and said control unit being configured to control the processor to process each image sample only within said two regions of interest to locate said opposite edges, wherein said processor repeatedly samples said image as said smoking article or filter rod is rotated by said rotating mechanism to obtain a plurality of image samples, wherein the processor processes each image sample to obtain a measurement of a diameter of said rolled smoking article or filter rod in each image sample, wherein the processor uses said measurements to obtain one or more physical properties of said rolled smoking article or filter rod selected from the mean diameter, ovality, circumference, roundness and shape of said rolled smoking article or filter rod, wherein said processor locates in each image sample two opposite edges of the rolled smoking article or filter rod in profile and calculates the distance between said opposite edges.

2. An apparatus for determining one or more physical properties of a rolled smoking article or filter rod, said rolled smoking article or filter rod having a longitudinal axis, said apparatus comprising:
   an imaging device defining a field of view disposed alone an optical axis, said imaging device imaging a rolled smoking article or filter rod in said field of view;
   a positioning unit which positions a smoking article or filter rod in said field of view such that the longitudinal axis of the smoking article or filter rod is substantially orthogonal to the optical axis of the imaging device;
   an illuminating unit which illuminates said field of view;
   a rotating mechanism which rotates said smoking article or filter rod about its longitudinal axis in said field of view;
   a processor which processes said image to determine one or more physical properties of a smoking article or filter rod in said field of view; and
   a control unit which controls said processor, said control unit comprising a database which stores data indicating the axial direction of a rolled smoking article which is axially asymmetric such that said rolled smoking article is directional, said processor repeatedly sampling said image as said rolled smoking article is rotated by said rotating mechanism, and processing each sample to detect the position of a shadow cast by a longitudinal seam of an outer layer of the rolled smoking article, said outer layer being wrapped circumferentially around said rolled smoking article to overlap itself thereby to form said seam, thereby to determine the direction of wrapping of said outer layer relative to the direction of the rolled smoking article, wherein said processor repeatedly samples said image as said smoking article or filter rod is rotated by said rotating mechanism to obtain a plurality of image samples, wherein the processor processes each image sample to obtain a measurement of a diameter of said rolled smoking article or filter rod in each image sample, wherein the processor uses said measurements to obtain one or more physical properties of said rolled smoking article or filter rod selected from the mean diameter, ovality, circumference, roundness and shape of said rolled smoking article or filter rod.

3. Apparatus as claimed in claim 2, wherein said database stores a nominal width of said rolled smoking article, and said control unit derives two laterally spaced regions of interest of said field of view based on said nominal width, each of said regions of interest encompassing all likely positions of said shadow depending on the direction of wrapping of said outer later, and controls said processor to detect the presence of said shadow only in one of said regions of interest.

4. Apparatus as claimed in claim 2, wherein said illuminating unit comprises sidelights positioned obliquely relative to the optical axis to enhance the shadow cast by said seam.

5. Apparatus as claimed in claim 2, wherein said processor determines the respective wrapping directions of two or more outer layers of a rolled smoking article, each of which outer layers is wrapped circumferentially around the rolled smoking article to overlap itself to form an axially extending seam.

6. A method of determining one or more physical properties of a rolled smoking article or filter rod, said rolled smoking article or filter rod having a longitudinal axis, said method comprising:
   disposing a rolled smoking article or filter rod within a field of view defined along an optical axis of an imaging means such that the longitudinal axis of the smoking article or filter rod is substantially orthogonal to the optical axis of the imaging means;
   illuminating said field of view;
   imaging said rolled smoking article or filter rod within said field of view to form a digital image;
   rotating said smoking article or filter rod about its longitudinal axis in said field of view;
   repeatedly sampling said image as said smoking article or filter rod is rotated to obtain a plurality of image samples;

electronically processing each image sample to obtain a measurement of a diameter of said rolled smoking article or filter rod in each image sample;

electronically processing said measurements to obtain one or more physical properties of said rolled smoking article or filter rod selected from the mean diameter, ovality, circumference, roundness and shape of said rolled smoking article or filter rod;

determining the diameter of the rolled smoking article or filter rod in each image sample by processing the image sample to locate the two opposite edges of the rolled smoking article or filter rod in profile and calculating the distance between said opposite edges; and processing each image sample within two predetermined, laterally spaced regions of interest of said field of view to locate said two opposite edges, which regions of interest are determined on the basis of the nominal diameter of the rolled smoking article or filter rod.

7. A method of determining one or more physical properties of a rolled smoking article or filter rod, said rolled smoking article or filter rod having a longitudinal axis, said method comprising:

disposing a rolled smoking article or filter rod within a field of view defined along an optical axis of an imaging means such that the longitudinal axis of the smoking article or filter rod is substantially orthogonal to the optical axis of the imaging means;

illuminating said field of view;

imaging said rolled smoking article or filter rod within said field of view to form a digital image;

rotating said smoking article or filter rod about its longitudinal axis in said field of view;

repeatedly sampling said image as said smoking article or filter rod is rotated to obtain a plurality of image samples;

electronically processing each image sample to obtain a measurement of a diameter of said rolled smoking article or filter rod in each image sample;

electronically processing said measurements to obtain one or more physical properties of said rolled smoking article or filter rod selected from the mean diameter, ovality, circumference, roundness and shape of said rolled smoking article or filter rod; and determining an axial direction of a rolled smoking article which is axially asymmetric such that said rolled smoking article is directional and comprises at least one outer layer which is wrapped circumferentially around said rolled smoking article to overlap itself thereby to form a longitudinal seam, and processing said image samples to determine the wrapping direction of said outer layer relative to the direction of said rolled smoking article.

8. A method as claimed in claim 7, wherein said image samples are processed to determine the position of said longitudinal seam by detecting the position of a shadow cast by said seam as the rolled smoking article rotates.

9. A method as claimed in claim 8, including processing each image sample to detect the presence of said shadow in two predetermined, laterally spaced regions of interest being determinative of the direction of wrapping of the outer layer, the regions of interest being determined on the basis of a predetermined nominal width of the rolled smoking article.

10. A method as claimed in claim 8, including illuminating said rolled smoking article obliquely to enhance the shadow cast by said seam.

11. A method as claimed in claim 8, wherein said rolled smoking article comprises two or more outer layers, each of which outer layers is wrapped circumferentially around the rolled smoking article to overlap itself to form an axially extending seam, and said image is processed to determine the wrapping direction of each outer layer relative to the direction of the roiled smoking article.

* * * * *

UNITED STATES PATENT AND TRADEMARK OFFICE
CERTIFICATE OF CORRECTION

PATENT NO. : 7,580,137 B2 Page 1 of 1
APPLICATION NO. : 10/549995
DATED : August 25, 2009
INVENTOR(S) : Ronald Frederick Wilson It is certified that error appears in the above-identified patent and that said Letters Patent is hereby corrected as shown below:

In Claim 11, column 36, line 36, please change "roiled smoking article" to --rolled smoking article--.

Signed and Sealed this

Eighth Day of December, 2009

David J. Kappos
*Director of the United States Patent and Trademark Office*